United States Patent
Oike et al.

(10) Patent No.: US 11,235,073 B2
(45) Date of Patent: Feb. 1, 2022

(54) METHOD FOR TREATING OR PREVENTING HEART FAILURE

(71) Applicant: NATIONAL UNIVERSITY CORPORATION KUMAMOTO UNIVERSITY, Kumamoto (JP)

(72) Inventors: Yuichi Oike, Kumamoto (JP); Tian Zhe, Kumamoto (JP); Tsuyoshi Kadomatsu, Kumamoto (JP); Keishi Miyata, Kumamoto (JP); Haruki Horiguchi, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 0 days.

(21) Appl. No.: 16/826,984

(22) Filed: Mar. 23, 2020

(65) Prior Publication Data
US 2020/0345866 A1 Nov. 5, 2020

Related U.S. Application Data

(62) Division of application No. 15/773,466, filed as application No. PCT/JP2016/082673 on Nov. 2, 2016, now abandoned.

(30) Foreign Application Priority Data

Nov. 6, 2015 (JP) .................................. 2015-218507
Jun. 22, 2016 (JP) .................................. 2016-123615

(51) Int. Cl.
| | |
|---|---|
| C12N 15/11 | (2006.01) |
| A61K 48/00 | (2006.01) |
| C12Q 1/6883 | (2018.01) |
| A61K 31/713 | (2006.01) |
| A61K 31/7105 | (2006.01) |
| C12N 15/113 | (2010.01) |
| A61P 9/10 | (2006.01) |
| C12N 15/864 | (2006.01) |

(52) U.S. Cl.
CPC .......... *A61K 48/005* (2013.01); *A61K 31/713* (2013.01); *A61K 31/7105* (2013.01); *A61P 9/10* (2018.01); *C12N 15/11* (2013.01); *C12N 15/113* (2013.01); *C12N 15/8645* (2013.01); *C12Q 1/6883* (2013.01); *A01K 2217/05* (2013.01); *A01K 2217/075* (2013.01); *A01K 2227/105* (2013.01); *A01K 2267/0375* (2013.01); *C12N 2310/14* (2013.01); *C12N 2750/14143* (2013.01); *C12Q 2600/158* (2013.01)

(58) Field of Classification Search
CPC . C12N 15/111; C12N 15/113; C12N 2310/14; A61P 9/10
See application file for complete search history.

(56) References Cited

U.S. PATENT DOCUMENTS

| | | | | |
|---|---|---|---|---|
| 2011/0098338 A1* | 4/2011 | Hajjar | ................. | A61K 48/005 |
| | | | | 514/44 A |
| 2013/0123339 A1* | 5/2013 | Heyes | .................... | C12N 15/88 |
| | | | | 514/44 A |

FOREIGN PATENT DOCUMENTS

| | | |
|---|---|---|
| JP | 2008531631 A | 8/2008 |
| JP | 2010535246 A | 11/2010 |
| JP | 2011093896 A | 5/2011 |
| WO | 2006094703 A1 | 9/2006 |
| WO | 2009018492 A2 | 2/2009 |
| WO | 2011071027 A1 | 6/2011 |

OTHER PUBLICATIONS

Gao et al., ANGPTL2 promotes tumor metastasis in hepatocellular carcinoma, Journal of Gastroenterology and Hepatology, vol. 30, pp. 396-404. (Year: 2015).*
White et al., Latent development of occlusive coronary atherosclerosis as a cause of decompensation of non-ischemic dilated cardiomyopathy, Cardiology, vol. 112, pp. 69-73. (Year: 2009).*
Bentzon et al., Red wine does not reduce mature atherosclerosis in apolipoprotein E-deficient mice, Circulation, vol. 103, pp. 1681-1687. (Year: 2001).*
Kadomatsu, Tsuyoshi et al., "Diverse roles of ANGPTL2 in physiology and Pathophysiology" Trends Endocrinol Metab, vol. 25, pp. 245-254, 2014.
Tabata, Mitsuhisa et al., "Angiopoietin-like Protein 2 Promotes Chronic Adipose Tissue inflammation and Obesity-related Systemic insulin resistance" Cell Metab, vol. 10, pp. 178-188, 2009.
Tazume, Hirokazu et al., "Macrophage-Derived Angiopoietin-like Protein 2 Accelerates Development of Abdominal Aortic Aneurysm" Arterioscler Thromb Vase Biol, vol. 32, pp. 1400-1409, 2012.
Tian, Zhe et al., "Perivascular adipose tissue-secreted angiopoietin-like protein 2 (Angpt12) Accelerates neointimal Hyperplasia after Endovascular injury" J. Mol Cell Cardiol, vol. 57, pp. 1-12, 2013.
Horio, Eiji et al., "Role of Endothelial Cell-Derived Angpt12 in Vascular inflammation Leading to Endothelial Dysfunction and Atherosclerosis Progression" Arterioscler Thromb Vase Biol, vol. 32, pp. 790-800, 2014.

(Continued)

Primary Examiner — Dana H Shin
(74) Attorney, Agent, or Firm — Hunton Andrews Kurth LLP

(57) ABSTRACT

A pharmaceutical composition can be provide for treating or preventing heart failure. Additionally, siRNA and a vector expressing said siRNA can be provided that can be used in the pharmaceutical composition for treating or preventing heart failure. For example, a pharmaceutical composition can be provided for treating or preventing heart failure that contains a DNA sequence encoding RNA containing a sense strand sequence of consecutive 18 to 29 nucleotides from angiopoietin-like protein 2 (ANGPTL2) mRNA or the alternative splicing type RNA thereof and an antisense strand sequence complementary to the sense strand sequence under control of a promoter, and a pharmaceutically acceptable carrier.

13 Claims, 13 Drawing Sheets
Specification includes a Sequence Listing.

(56) References Cited

OTHER PUBLICATIONS

Aoi, Jun et al., "Angiopoietin-like Protein 2 is a Important Facilitator of Inflammator Carcinogenesis and Metastasis" Cancer Res, vol. 71 pp. 7502-7512, 2011.

Endo, Motoyoshi et al., "Tumor Cell-Derived Angiopoietin-like Protein ANGPTL2 is a Critical Driver of Metastasis" Cancer Res, vol. 72, pp. 1784-1784, 2012

Odagiri, Haruki et al., "The Secreted Protein ANGPTL2 Promotes Metastasis of Osteosarcoma Cells . . . " Sci Signal, vol. 7, Issue 309, ra7, pp. 1-15, 2014.

Huang, Chi-Lun et al., "Serum Angiopoietin-Like Protein 2 Concentrations are Independently Associated with Heart Failure" Plos One, vol. 10, No. 9, Article No. e0138678/1-e0138678/11, Sep. 2015.

Tian, Zhe et al., Cardiac Vascular Endothelial Cell-Secreted Angiopoietin-Like Protein 2 (Angpt 2) Promotes Heart Failure in Murine Left Ventricular Pressure-Overload Model, Circulation Journal, vol. 79, Supplement 1 (CD-ROM), Article No. 1-3 (PJ-094), Mar. 2015.

Kim, I. et al., *Homo sapiens* angiopoietin-related protein-2 mRNA, complete cds., Genbank [From the Internet]; National Center for Biotechnology Information, Bethesda MD, USA, :http://www.ncbi.nlm.nih.gov/nuccore/AFI25175, Accession No. AFI25175, Sep. 1999.

Zincarelli, Carmela et al., Comparative Cardiac Gene Delivery of Adeno-Associated Virus Serotypes 1-9 reveals that AAv6 Mediates the Most Efficient Transduction in Mouse Heart, Clin Transi Sci., vol. 3, Issue 3, pp. 81-89, 2010.

Tian, Zhe et al., ANGPTL2 activity in cardiac pathologies accelerates hear failure by perturbing cardiac function and energy metabolism, Nature Comm. DOI:10.138/ncomms13016, pp. 1-19, Sep. 28, 2016.

International Search Report dated Feb. 7, 2017 for International Application No. PCT/JP2016/082673.

(NPL10) Matsubara, J. Kumamoto University Science Repository [From the Internet]; http://www.reposit.lib.kumamoto-u.ac.jp/bitstream/2298/21644/3/22-1774.pdf, pp. 1-52, Mar. 25, 2011 and English Language Abstract.

(NPL15) National University Corporation Kumamoto University, Shinfuzen no Aratana Hassho Mehcanism Kaimei to Shinki Idenshi Chiryo no Kaihatsu, Press Release [From the Internet], http://www.kumamoto-u.ac.jp/daigakujouhou/pressrelease/2016-file/release160928.pdf, Sep. 28, 2016 and English Language Abstract.

(NPL 17) International Preliminary Report on Patentability dated Jan. 2015 for International Application PCT/JP2016/082673 and English Language Translation.

* cited by examiner

FIG. 2b                    FIG. 2c

FIG. 4a    FIG. 4b    FIG. 4c
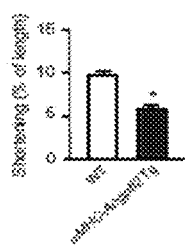 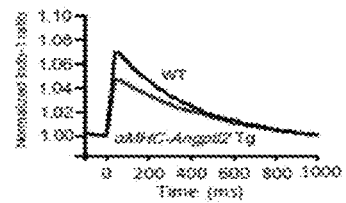 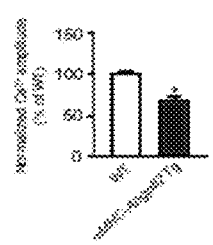
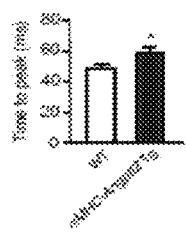 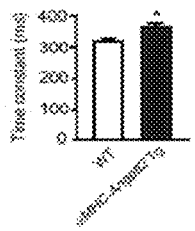 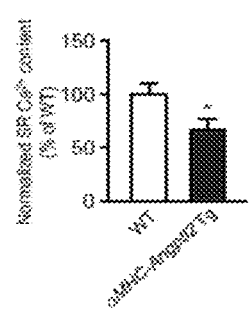
FIG. 4d    FIG. 4e    FIG. 4f
FIG. 5
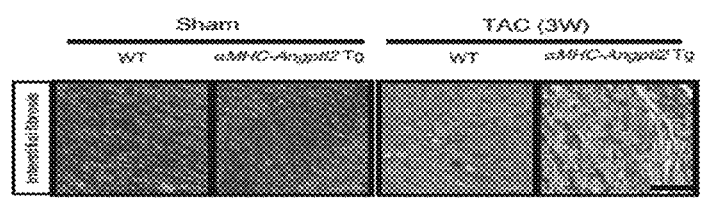

FIG. 14
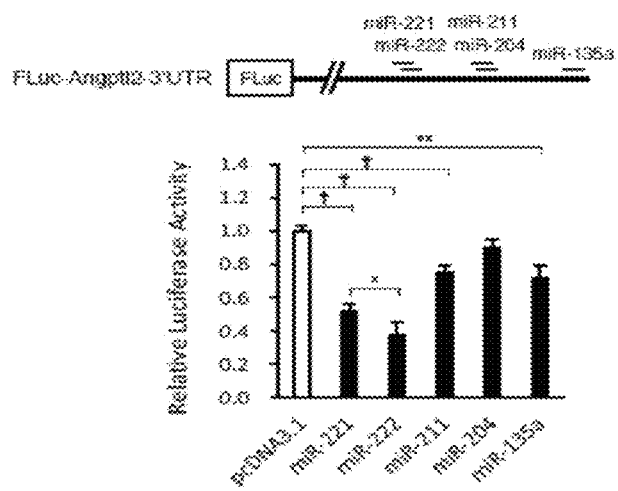
FIG. 15a
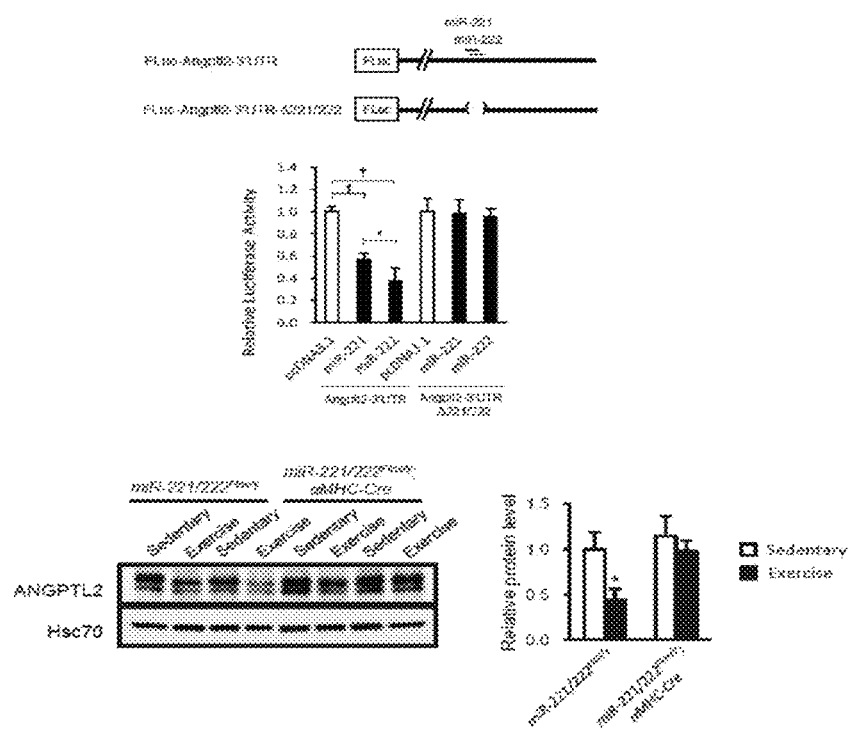
FIG. 15b

FIG. 18
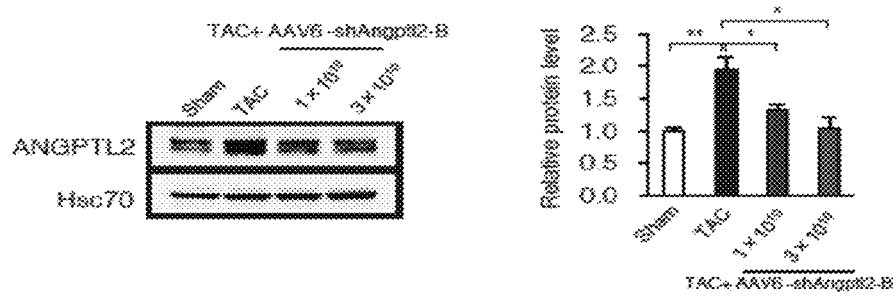
FIG. 19a
FIG. 19b
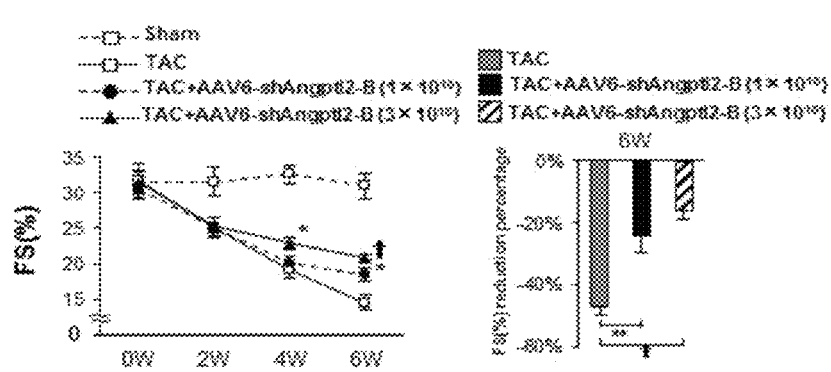
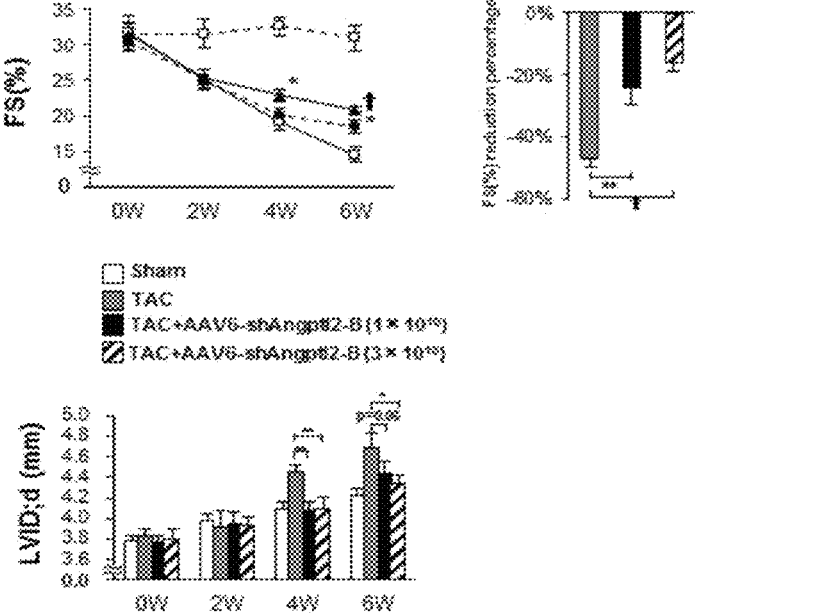
FIG. 19c

FIG. 22b                    FIG 22c siANGPTL2 sequences

A: GGAACAUUGACGGCGAAUATT
B: GAGAGUUCAUUUACCUAAATT
C: GGCUCUUACUCACUCAAGATT
D: GGCAUUGUGAGCGAGGUGATT
E: GCCAUUACCGGAGCCGCUATT
F: GUUUCCGCCUGGAACCUGATT
G: GAAACUGUGCCCACUACCATT

FIG. 24

```
GGGGCCTGCCGAGGCCGCCAAAGCGGGCTGGCCGGGAGGGGCCAGGCCAGCTGGGGCCGGAG
CTCGTGTGACATCACCGGGCGGCCCGCCTCTGTCTGGGGCTGAGGGGAGGCCCGGAGCCTTTCT
GGGGCCTGGGGGATCCTCTTGCACTGGTGGGTGGAGAGAAGCCGCCTGCAGCCAACCAGGGTCA
GGCTGTGCTCACAGTTTCCTCTGGCCGGCATGTAAAGGCTCCACAAAGGAGTTGGGAGTTCAAAT
GAGGCTGCTGCGGACGGCCTGAGGATGGACCCCAAGCCCTGGACCTGCCGAGCGTGGCACTGA
GGCAGCGGCTGACCCTACTGTGAGGGAAAGAAGGTTGTGAGCAGCCCCGCAGGACCCCTGGCC
AGCCCTGGCCCCAGCCTCTCCCGGAGCCCTCTGTGGAGGCAGAGCCAGTGGAGCCCAGTGAGG
CAGGGCTGCTTGGCAGCCACCGGGCCTGCAACTCAGGAACCCCTCCAGAGGCCATGGACAGGCT
GCCCCGCTGACGGCCAGGGTGAAGCATGTGAGGAGCCGCCCCGGAGCCAACCAGGAGGGAAGA
GGCTTTCATAGATTCTATTCACAAGCAATAACCACCATTTGCAAGCACTGTTGCCGTTACTGTGC
GTGACATGCTGATGGCTCGGACTGCTGGCGTGCCATGGGAGCTGTTGCAGGCCAGGAGGACGGT
TTTGAGGGCACTGAGGAGGGCTCGCCAAGAGGAGTTCATTTACCTAAACAGGTACAAGCGGGCGG
GCGAGTCCCAGGACAAGTGCACCTACACCTTCATTGTGCCCCAGCAGCGGGTCACGGGTGCCAT
CTGCGTCAACTCCAAGGAGCCTGAGGTGCTTCTGGAGAACCGAGTGCATAAGCAGGAGCTAGAG
CTGCTCAACAATGAGCTGCTCAAGCAGAAGCGGCAGATCGAGACGCTGCAGCAGCTGGTGGAG
GTGGACGGCGGCATTTTCACCAACGTTGAAGCTGCTGCGCAAGGAGAGCCCCAACATGAACTCG
CGGGTCACGCAGCTCTACATGCAGCTCCTGCACGAGATCATCCGCAAGCGGGACAACGCGTTGG
AGCTCTCCCAGCTGGAGAACAGGATCCTGAACCAGACAGCCGACATGCTGCAGCTGGCCAGCAA
GTACAAGGACCTGGAGCACAAGTACCAGCACCTGGCCACACTGGCCCACAACCAATCAGAGATC
ATCGCGCAGCTTGAGGACACTGCCAGAGGGTGCCCTCGGCCAGGCCCGTCCCCAGCCACCC
CCCGCTGCCCCGCCCCGGGTCTACCAACCACCCACCTACAACCGCATCATCAACCAGATCTCTAC
CAACGAGATCCAGAGGTGACCAGAACCTGAAGGTGCTGCCACCCCCTCTGCCCACTATGCCCACT
CTCACCAGCAGCTCCCATCTTCCACCGACAAGCCGTCGGGCCCATGGAGAGACTGCCTGCAGGCCC
TGGAGGATGGCCACGACACCAGCTCCATCTACCTGGTGAAGCCGGAGAACACCAACCCGCCTCAT
GCAGGTGTGGTCGACCAGAGACACGACCCCCGGGGCTGGACCGTCATCCAGAGACGCCTGA
TGGCTCTGTTAACTTCTTCAGGAACTGGGAGACGTACAAGCAAGGGTTTGGGAAACATTTACCCA
GAATCCTGGCTGGGCCCTGGAGAACATTTACTGGCTGACGAACCAAGGCAACTACAAACTCCTGG
TGACCATGGAGGACTGGTCCGGCCGCAAAGTCTTTGCAGAATACGCCAGTTTCCCCCTTGAACC
TGAGAGCCAGTATTATAAGCTGCCGCTGGGGCCTCACATGGCAATGCGGGTGACTCCTTACAT
GGCACAAGCGGCAAGCAGTTCACCACCCCTGGACAGAGATCATGATGTCTACACAGGAAACTGTGC
CCACTACCAGAAGGGAGGCTGGTGGTATAACGCCTGTGCCCACTCCAACCCTCAACGGGGTCTGG
TACCCCCGGGCGGCATTAGCGAGACCCGCTGCCAGGACGGAGTCTACTGGGCTGAGTTCCGAGGAG
GCTCTTTTCTCACTCAACAAAGTGGTGATGATGATCGACCGAACCCCAACACCTTTCCACTATC
AGCTACCCTTCCTCACCTCTCGTGGCCATGGCCAGGTCCCACCCTGGTCAGCGTGGCCACAGC
ACAAAGAACAACTCCTCACCAGTTCATCCTGAGGCTGGGAGGACCGGGATGCTGGATTCTGTTT
TCCGAAGTCACTGCAGCGGATGATGGAACTGAATCGATACGGTGTTTTCTGTCCCTCCTACTTTC
CTTCACACCAGACAGCCCCTCATGTCTCCAGGACAGGACAGGACTACAGACAGTTTCTTTAA
ATAAATTAAGTCTCTACAATAAAAACACAACTGCAAAGTACCTTCATAATATACATGTGTATGAGC
CTCCCTTGTGCACGTATGTGTATCCACATATATATGCATTTAGATATACATCACATGTGATATATCT
AGATCCATATATAGGTTTCCCTTAGATACCTAAATACACATATATTCAGTTCTCAGATGTTGAAGCT
GTCACCAGCAGCTTTGCTCTTAGGAGAAAAGCATTTCATTAGTGTTGTATTACTTGAGTCTAAGG
GTAGATCACAGACTGTGTGGTCTCAACTGAAAGGATCACCCTTGGCATCTGTGTGCCTGGATTGT
TCCAGAATGTCTACAATGCTAATCTCTCACATAAGGGTTCCCAGCTTCTTAAGACCCCTTTGGC
ACCTAATCAAATTTCAAAATCCCTCCCCCCACATTTTCATACTTTTCCCCATTCTCAGGACTTTTCA
CCATCCATCACCCACTTATCCCTTCATTTGACACCATTCATTAAGTGCCTTCTGTGTGTCAGTCCC
TGGCCACTCACTGCAGTTCAAGGCCCCCTTTCCGCTCTGCTGTACTCCTCGCCTACCTACTCCTT
GCCTTTTCTGTGCACAGCCCCTTCTTTCCAGGCGAGATTCCTCAGCTTCTGAGTAGGAAACACT
CCGGGCTCCAGGTTTCTGGTTGGGAAGGGAAGGCCAGGCCAAAAGCTCCACCGGCCGTATAGAT
AATGTACTCGCAGTTTTGTATCTTCCATTCATACTTTAACCTACAGGTCATTTGAGTCTTCACACA
AATAATAACCTAICTGGCCAGGAGAATTAICTCAGAACAGAAGTCATCAGATCATCAGAGCCCCC
AGATGGCTACAGACCAGAGATTCCACGCTCTCAGGCTGACTAGAGTCCGCATCTCATCTCCAAAC
TACACTTCCCTGGAGAACAAGTGCCACAAAAATGAAAACAGGCCACTTCTCAGGAGTTGAATAAT
CAGGGGTCACGGACCCCTTGGTTGATCACTGCAGCATGGTGGCTTTCTGAGTCCTGTTGGCC
ACCAAGTGTCAGCCTCAGCACTCCCGGGACTATTGCCAAGAAGGGCAAGGGATGAGTCAAGAA
GGTGAGACCCTTCCCGGTGGGCACGTGGGCCAGGCTGTGTGAGATGTTGGATGTTGGTACTGT
CCATGTCTGGGTGTGTGCCTATTACCTCAGCATTTCTCACAAAGTGTACCATGTAGCATGTTTGT
GTATATAAAAGGGAGGGTTTTTTAAAAATATATTCCCAGATTATCCTTGTAATGACACGAATCTG
CAATAAAAGCCATCAGTGCTATTTGGATGTATCTACA
```

METHOD FOR TREATING OR PREVENTING HEART FAILURE

CROSS-REFERENCE TO RELATED APPLICATIONS

The present application is a divisional of U.S. application Ser. No. 15/773,466 filed May 3, 2018, which is U.S. national phase application and claims priority to PCT Application No. PCT/JP2016/082673 filed on Nov. 2, 2016 and published on May 11, 2017 as International Publication No. WO 2017/078100, and also claims priority from Japanese Patent Application Nos. 2015-218507 and 2016-123615, filed on Nov. 6, 2015 and Jun. 22, 2016, respectively. The entire disclosures of such application are incorporated herein by reference.

TECHNICAL FIELD

The present invention relates to a novel pharmaceutical composition for treating or preventing heart failure. Particularly, the present invention relates to a pharmaceutical composition for treating or preventing heart failure by molecularly-targeting the gene of angiopoietin-like protein 2 (ANGPTL2).

BACKGROUND ART

Along with the arrival of an aging society, the number of heart failure patients increases, and once affected with heart failure, it is a major obstacle to the realization of healthy and longevity society such as lowering of the quality of life, also it becomes a big problem both medically and socially. For severe heart failure, there is no effective treatment other than invasive therapeutic methods such as ventricular assist device (VAD) and cardiac resynchronization therapy (CRT) by inserting a pacemaker.

Cardiac hypertrophy is an adaptive response to increased workload such as hypertension, and often progresses to heart failure. Heart failure is a leading cause of death and there are over 23 million patients with heart failure worldwide. Heart failure can be defined as an imbalance between peripheral oxygen supply and demand resulting from cardiac dysfunction. Decreased cardiac contractility causes heart failure with reduced ejection fraction (HFrEF). By contrast, in heart failure associated with preserved ejection fraction (HFpEF), contractile function appears normal despite the presence of symptoms and heart failure is thought to be caused by abnormal diastolic function. Both contraction and relaxation are major energy-consuming processes, suggesting that failure of myocardial energy metabolism underlies both HFrEF and HFpEF. However, how cardiac function and myocardial energy metabolism are depressed during heart failure development remains unclear.

Cardiac hypertrophy, defined as an increase in heart mass due to cardiomyocyte enlargement, is an adaptive response to increased workload and a means to maintain cardiac function. Pathological stimuli, such as hypertension, promote the transition from hypertrophy to heart failure, a condition associated with cardiac fibrosis and re-expression of a fetal cardiac gene program. By contrast, exercise induces physiological hypertrophy characterized by preserved myocardial structure and energy metabolism, protecting the heart from heart failure. Mechanistic differences between both types of hypertrophy remain unclear.

In heart failure, protein expression of SERCA2 which is important for maintenance of cardiac function is reported to be decreased. Because of this, clinical trials of AAV6-SERCA2 gene therapy using an adeno-associated virus serotype 6 (AAV6) as a means for delivery to the myocardium in vivo have been performed for the purpose of increasing the protein amount of SERCA2 in the heart, currently, as a treatment for heart failure, and good results have been reported in cardiac function recovery and life prognosis.

Angiopoietin-like protein (ANGPTL) is a secretory protein structurally similar to angiopoietin which is an angiogenic factor, and seven ANGPTLs have been identified so far. ANGPTL2 is known to act on vascular cells and monocytes, in addition, it is known that ANGPTL3 and ANGPTL4 play an important role in lipid metabolism, and AGF (Angiopoietin-like growth factor)/ANGPTL6 play an important role in metabolism of energy and sugar. A variety of physiological effects of such ANGPTL family are attracting attention as a new therapeutic target for lifestyle-related diseases such as metabolic syndromes and cancers. Recently, it has been reported that the concentration of ANGPTL2 in blood increases in obesity and in a severe insulin resistance, and in diabetic patients and arteriosclerosis patients.

To date, previous studies identified a role for ANGPTL2 in chronic inflammation associated with obesity diabetes, atherosclerotic disease, and cancer progression (e.g., Patent Document 1, Non-Patent Documents 1 to 8). However, function of the signaling factor angiopoietin-like protein 2 (ANGPTL2) in heart remains unknown.

CITATION LIST

Patent Document

Patent Document 1: Japan Unexamined Patent Application Publication No. 2011-93896

Non-Patent Document

Non-Patent Document 1: Kadomatsu, T., et al. Trends Endocrinol Metab 25, 245-254 (2014).
Non-Patent Document 2: Tabata, M., et al. Cell Metab 10, 178-188 (2009).
Non-Patent Document 3: Tazume, H., et al. Arterioscler Thromb Vasc Biol 32, 1400-1409 (2012).
Non-Patent Document 4: Tian, Z., et al. J Mol Cell Cardiol 57, 1-12 (2013).
Non-Patent Document 5: Horio, E., et al. Arterioscler Thromb Vasc Biol 34, 790-800 (2014).
Non-Patent Document 6: Aoi, J., et al. Cancer Res 71, 7502-7512 (2011).
Non-Patent Document 7: Endo, M., et al. Cancer Res 72, 1784-1794 (2012).
Non-Patent Document 8: Odagiri, H., et al. Sci Signal 7, ra7 (2014).

SUMMARY OF THE INVENTION

Technical Problem

It is an object of the present invention to provide a new pharmaceutical composition for treating or preventing heart failure.

Another object of the present invention is to provide a siRNA which can be used in a pharmaceutical composition for the treatment or prevention of heart failure, and a vector capable of expressing the siRNA.

Further, another object of the present invention is to provide a method for selecting a subject to which the pharmaceutical composition of the present invention is applied and a method for confirming the effect of the pharmaceutical composition of the present invention.

Solution to Problem

The present inventors have found that angiopoietin-like protein 2 (ANGPTL2) is expressed in cardiac tissues such as cardiomyocytes and microvascular endothelial cells and its expression is increased significantly in angiotensin II (Ang II)-induced mouse cardiac hypertrophy models and transverse aorta constriction (TAC)-induced mouse cardiac hypertrophy/heart failure models, and that its expression is increased also in human heart failure patients compared with healthy hearts, and found that ANGPTL2 plays some role in pathological heart. Then, as a result of preparation and analysis of genetically engineered mice, it was confirmed that ANGPTL2 overexpressing mice showed cardiac dysfunction and further showed susceptibility to the development of heart failure. Conversely, ANGPTL2-deficient mice showed cardiac function enhancement and resistance to heart failure development, confirming that ANGPTL2 suppresses cardiac function, and facilitates pathologic cardiac hypertrophy and heart failure development.

As a result of detailed mechanism analysis, it was found that ANGPTL2 expression was increased during pathological cardiac hypertrophy, resulting in reducing the protein amount of SERCA2 which is important for maintenance of cardiac function by promoting the degradation of AKT, further suppressing heart energy metabolism pathway, and conversely, suppression of expression of ANGPTL2 caused an increase in the protein amount of SERCA2 via stabilization of AKT, caused heart energy metabolic pathway activation, and acted antagonistically on development of heart failure.

Furthermore, using rat neonatal cardiomyocyte culture and human iPS-derived cardiomyocytes, it was confirmed that the siRNA targeting ANGPTL2 significantly reduced the expression level of mRNA and protein of ANGPTL2 in cardiomyocytes and caused AKT-SERCA2 pathway activation and heart energy metabolism pathway activation.

Based on the above, the present inventors have found that suppression of the action of ANGPTL2 by using siRNA targeting ANGPTL2 gives a new pharmaceutical composition for treatment and prevention of heart failure, thus completing the present invention.

The present invention includes the following embodiments.

[1] A pharmaceutical composition for treating or preventing heart failure, comprising an expression vector containing a DNA sequence encoding RNA containing a sense strand sequence of consecutive 18 to 29 nucleotides (preferably 19 to 27 nucleotides, more preferably 19 to 25 nucleotides, further preferably 19 to 23 nucleotides) from angiopoietin-like protein 2 (ANGPTL2) mRNA or its alternative splicing type RNA and an antisense strand sequence as its complementary sequence under control of a promoter, and a pharmaceutically acceptable carrier, characterized in that when siRNA containing the above-described sense strand sequence and the above-described antisense strand sequence is transduced into an animal cell (preferably, a human cell), expression of the angiopoietin-like protein 2 gene in the cell is suppressed and a silencing effect on the angiopoietin-like protein 2 gene is produced.

[2] The pharmaceutical composition according to [1], wherein the above-described DNA sequence contains the above-described sense strand sequence, the above-described antisense strand sequence and a sequence encoding a hairpin type RNA composed of a single strand loop sequence (hairpin sequence) bonding the above-described sense strand sequence and the above-described antisense strand sequence via covalent bond, and the hairpin sequence is processed by Dicer, an intracellular RNase, to form siRNA containing the above-described sense strand sequence and the above-described antisense strand sequence.

[3] The pharmaceutical composition according to [1] or [2], wherein the above-described sense strand sequence is a nucleotide sequence shown by any one of the following SEQ ID NO. 2 to SEQ ID NO. 8 or a sequence obtained by substitution, deletion or addition of one base in the nucleotide sequence:

```
SEQ ID NO. 2:
GGAACAUUGACGGCGAAUA

SEQ ID NO. 3:
GAGAGUUCAUUUACCUAAA

SEQ ID NO. 4:
GGCUCUUACUCACUCAAGA

SEQ ID NO. 5:
GGCAUUGUGAGCGAGGUGA

SEQ ID NO. 6:
GCCAUUACCGGAGCCGCUA

SEQ ID NO. 7:
GUUUCCGCCUGGAACCUGA

SEQ ID NO. 8:
GAAACUGUGCCCACUACCA.
```

[5] The pharmaceutical composition according to [1] or [2], wherein the above-described DNA sequence contains a nucleotide sequence shown by any one of the following SEQ ID NO. 9 to SEQ ID NO. 15 or a sequence obtained by substitution, deletion or addition of one base in the nucleotide sequence:

```
SEQ ID NO. 9:
GGAACATTGACGGCGAATA

SEQ ID NO. 10:
GAGAGTTCATTTACCTAAA

SEQ ID NO. 11:
GGCTCTTACTCACTCAAGA

SEQ ID NO. 12:
GGCATTGTGAGCGAGGTGA

SEQ ID NO. 13:
GCCATTACCGGAGCCGCTA

SEQ ID NO. 14:
GTTTCCGCCTGGAACCTGA

SEQ ID NO. 15:
GAAACTGTGCCCACTACCA.
```

[5] The pharmaceutical composition according to any one of [1] to [4], wherein the above-described expression vector is a plasmid or a viral vector.

[6] The pharmaceutical composition according to [5], wherein the above-described viral vector is an adenoviral vector, an adeno-associated viral vector, a lentiviral vector or a retroviral vector.

[7] The pharmaceutical composition according to [6], wherein the above-described viral vector is an adeno-associated virus serotype 6 (AAV6) vector.

[8] A pharmaceutical composition for treating or preventing heart failure, comprising siRNA containing a sense strand sequence of consecutive 18 to 29 nucleotides (preferably 19 to 27 nucleotides, more preferably 19 to 25 nucleotides, further preferably 19 to 23 nucleotides) from angiopoietin-like protein 2 (ANGPTL2) mRNA or its alternative splicing type RNA and an antisense strand sequence as its complementary sequence, and a pharmaceutically acceptable carrier, characterized in that when siRNA containing the above-described sense strand sequence and the above-described antisense strand sequence is transduced into an animal cell (preferably, a human cell), expression of the angiopoietin-like protein 2 gene is suppressed and a silencing effect on the angiopoietin-like protein 2 gene is produced.

[9] The pharmaceutical composition according to [8], wherein the above-described sense strand sequence contains a nucleotide sequence shown by any one of the following SEQ ID NO. 2 to SEQ ID NO. 8 or a sequence obtained by substitution, deletion or addition of one base in the nucleotide sequence:

SEQ ID NO. 2:
GGAACAUUGACGGCGAAUA

SEQ ID NO. 3:
GAGAGUUCAUUUACCUAAA

SEQ ID NO. 4:
GGCUCUUACUCACUCAAGA

SEQ ID NO. 5:
GGCAUUGUGAGCGAGGUGA

SEQ ID NO. 6:
GCCAUUACCGGAGCCGCUA

SEQ ID NO. 7:
GUUUCCGCCUGGAACCUGA

SEQ ID NO. 8:
GAAACUGUGCCCACUACCA.

[10] An agent for suppressing expression of angiopoietin-like protein 2 in an animal cell (preferably, a human cell), comprising an expression vector containing a DNA sequence encoding RNA containing a sense strand sequence of consecutive 18 to 29 nucleotides (preferably 19 to 27 nucleotides, more preferably 19 to 25 nucleotides, further preferably 19 to 23 nucleotides) from angiopoietin-like protein 2 (ANGPTL2) mRNA or its alternative splicing type RNA and an antisense strand sequence as its complementary sequence under control of a promoter, characterized in that when siRNA containing the above-described sense strand sequence and the above-described antisense strand sequence is transduced into an animal cell (preferably, a human cell), expression of the angiopoietin-like protein 2 gene in the cell is suppressed and a silencing effect on the angiopoietin-like protein 2 gene is produced.

[11] The agent for suppressing expression of angiopoietin-like protein 2 according to [10], wherein the above-described DNA sequence contains the above-described sense strand sequence, the above-described antisense strand sequence and a sequence encoding a hairpin type RNA composed of a single strand loop sequence (hairpin sequence) bonding the above-described sense strand sequence and the above-described antisense strand sequence via covalent bond, and the hairpin sequence is processed by Dicer, an intracellular RNase, to form siRNA containing the above-described sense strand sequence and the above-described antisense strand sequence.

[12] The agent for suppressing expression of angiopoietin-like protein 2 according to [10] or [11], wherein the above-described sense strand sequence is a base sequence shown by any one of the following SEQ ID NO. 2 to SEQ ID NO. 8 or a sequence obtained by substitution, deletion or addition of one base in the base sequence:

SEQ ID NO. 2:
GGAACAUUGACGGCGAAUA

SEQ ID NO. 3:
GAGAGUUCAUUUACCUAAA

SEQ ID NO. 4:
GGCUCUUACUCACUCAAGA

SEQ ID NO. 5:
GGCAUUGUGAGCGAGGUGA

SEQ ID NO. 6:
GCCAUUACCGGAGCCGCUA

SEQ ID NO. 7:
GUUUCCGCCUGGAACCUGA

SEQ ID NO. 8:
GAAACUGUGCCCACUACCA.

[13] The agent for suppressing expression of angiopoietin-like protein 2 according to [10] or [11], wherein the above-described DNA sequence contains a base sequence shown by any one of the following SEQ ID NO. 9 to SEQ ID NO. 15 or a sequence obtained by substitution, deletion or addition of one base in the base sequence:

SEQ ID NO. 9:
GGAACATTGACGGCGAATA

SEQ ID NO. 10:
GAGAGTTCATTTACCTAAA

SEQ ID NO. 11:
GGCTCTTACTCACTCAAGA

SEQ ID NO. 12:
GGCATTGTGAGCGAGGTGA

SEQ ID NO. 13:
GCCATTACCGGAGCCGCTA

SEQ ID NO. 14:
GTTTCCGCCTGGAACCTGA

SEQ ID NO. 15:
GAAACTGTGCCCACTACCA.

[14] The agent for suppressing expression of angiopoietin-like protein 2 according to any one of [10] to [13], wherein the above-described expression vector is a plasmid or a viral vector.

[15] The agent for suppressing expression of angiopoietin-like protein 2 according to [14], wherein the above-described viral vector is an adenoviral vector, an adeno-associated viral vector, a lentiviral vector or a retroviral vector.

[16] The agent for suppressing expression of angiopoietin-like protein 2 according to [15], wherein the above-described viral vector is an adeno-associated virus serotype 6 (AAV6) vector.

[17] A method for determining whether a subject is in need of treatment or prevention of heart failure with the pharmaceutical composition according to any one of [1] to [9] by measuring expression of angiopoietin-like protein 2 (ANGPTL2) in blood derived from a mammal (preferably, human) as the subject.

[18] The method according to [17], wherein the above-described blood is blood derived from a dilated cardiomyopathy (DCM) patient.

[19] The method according to [18], wherein the above-described blood is blood of the aortic root (Ao) and the coronary sinus (CS) of a dilated cardiomyopathy patient.

[20] The method according to [19], wherein when the expression level of angiopoietin-like protein 2 (ANGPTL2) in the blood of the coronary sinus (CS) is higher than the expression level in the blood of the aortic root (Ao), it is determined that the subject from which the blood is derived is in need of treatment or prevention of heart failure.

[21] A method in which when the expression level of angiopoietin-like protein 2 (ANGPTL2) in the blood of the coronary sinus (CS) is higher than the expression level in the blood of the aortic root (Ao), it is determined that the subject from which the blood is derived is a subject to which the pharmaceutical composition according to any one of [1] to [9] is to be administered.

[22] A method for determining whether the therapeutic effect of heart failure is obtained in a subject by measuring expression of angiopoietin-like protein 2 (ANGPTL2) in blood derived from the subject to which the pharmaceutical composition according to any one of [1] to [9] has been administered.

[23] The method according to [22], wherein the above-described blood is blood of the coronary sinus (CS) of the subject.

[24] The method according to [23], wherein expression of angiopoietin-like protein 2 (ANGPTL2) is measured before and after administration of the pharmaceutical composition according to any one of [1] to [9].

[25] A method for treating or preventing heart failure, comprising administering an expression vector containing a DNA sequence encoding RNA containing a sense strand sequence of consecutive 18 to 29 nucleotides (preferably 19 to 27 nucleotides, more preferably 19 to 25 nucleotides, further preferably 19 to 23 nucleotides) from angiopoietin-like protein 2 (ANGPTL2) mRNA or its alternative splicing type RNA and an antisense strand sequence as its complementary sequence under control of a promoter to a subject in need of treatment or prevention (preferably, human), and expressing and generating siRNA containing the above-described sense strand sequence and the above-described antisense strand sequence in an amount effective for treating or preventing heart failure of the subject, characterized in that the siRNA suppresses expression of the angiopoietin-like protein 2 gene in the cell in which the siRNA is expressed and generated, and produces silencing effect on the angiopoietin-like protein 2 gene.

[26] The method for treating or preventing heart failure according to [25], wherein the above-described DNA sequence contains the above-described sense strand sequence, the above-described antisense strand sequence and a sequence encoding a hairpin type RNA composed of a single strand loop sequence (hairpin sequence) bonding the above-described sense strand sequence and the above-described antisense strand sequence via covalent bond, and the hairpin sequence is processed by Dicer, an intracellular RNase, to form siRNA containing the above-described sense strand sequence and the above-described antisense strand sequence.

[27] The method for treating or preventing heart failure according to [25] or [26], wherein the above-described sense strand sequence is a base sequence shown by any one of the following SEQ ID NO. 2 to SEQ ID NO. 8 or a sequence obtained by substitution, deletion or addition of one base in the base sequence:

```
SEQ ID NO. 2:
GGAACAUUGACGGCGAAUA

SEQ ID NO. 3:
GAGAGUUCAUUUACCUAAA

SEQ ID NO. 4:
GGCUCUUACUCACUCAAGA

SEQ ID NO. 5:
GGCAUUGUGAGCGAGGUGA

SEQ ID NO. 6:
GCCAUUACCGGAGCCGCUA

SEQ ID NO. 7:
GUUUCCGCCUGGAACCUGA

SEQ ID NO. 8:
GAAACUGUGCCCACUACCA.
```

[28] The method for treating or preventing heart failure according to [25] or [26], wherein the above-described DNA sequence contains a base sequence shown by any one of the following SEQ ID NO. 9 to SEQ ID NO. 15 or a sequence obtained by substitution, deletion or addition of one base in the base sequence:

```
SEQ ID NO. 9:
GGAACATTGACGGCGAATA

SEQ ID NO. 10:
GAGAGTTCATTTACCTAAA

SEQ ID NO. 11:
GGCTCTTACTCACTCAAGA

SEQ ID NO. 12:
GGCATTGTGAGCGAGGTGA

SEQ ID NO. 13:
GCCATTACCGGAGCCGCTA

SEQ ID NO. 14:
GTTTCCGCCTGGAACCTGA

SEQ ID NO. 15:
GAAACTGTGCCCACTACCA.
```

[29] The method for treating or preventing heart failure according to any one of [25] to [28], wherein the above-described expression vector is a plasmid or a viral vector.

[30] The method for treating or preventing heart failure according to [29], wherein the above-described viral vector is an adenoviral vector, an adeno-associated viral vector, a lentiviral vector or a retroviral vector.

[31] The method for treating or preventing heart failure according to [30], wherein the above-described viral vector is an adeno-associated virus serotype 6 (AAV6) vector.

[32] A method for determining whether a subject is suffering from heart failure or at risk of developing heart failure by measuring expression of angiopoietin-like protein 2 (ANGPTL2) in blood from a mammal (preferably, human) as the subject.

[33] The method according to [32], wherein the above-described blood is blood of the aortic root (Ao) and/or the coronary sinus (CS).

[34] The method according to [33], wherein when the expression level of angiopoietin-like protein 2 (ANGPTL2) in the blood of the coronary sinus (CS) is higher than the expression level in the blood of the aortic root (Ao), it is determined that the subject from which the blood is derived is suffering from heart failure or at risk of developing heart failure.

Advantageous Effect of the Invention

According to the present invention, expression of the angiopoietin-like protein 2 gene in cardiomyocytes can be suppressed and a pharmaceutical composition which is effective for treatment or prevention of heart failure is provided.

BRIEF EXPLANATION OF THE DRAWINGS

FIG. 2a to FIG. 2c shows the results of confirming the expression of ANGPTL2 in GFP$^+$ cardiomyocytes and GFP$^-$ cardiomyocytes. FIG. 2a shows the results of analysis of ANGPTL2 and GFP using Western blot in GFP$^+$ cardiomyocytes and GFP$^-$ non-cardiomyocytes from Myh6-EGFP Tg mice. Hsc70 was served as a control. The value of GFP$^+$ was set to 1. The graph shows the mean of each group (n=3). FIG. 2b shows the results of quantitative RT-PCR analysis of expression of Angptl2 in GFP$^+$ and GFP$^-$ cells 6 weeks after the TAC treatment or sham-control treatment (Sham). It shows the mean of each group (n=3). Values from control were set to 1. FIG. 2c shows the results of quantitative RT-PCR analysis of expression of Angptl2 in GFP$^+$ and GFP$^-$ cells 2 weeks after the Ang II treatment or vehicle treatment. It shows the mean of each group (n=3). Values from control were set to 1. Data are expressed as the mean±SEM. *: $p<0.05$.

FIG. 4a to FIG. 4f shows the results of evaluating the excitation contraction (EC) coupling of cardiomyocytes using single cells isolated from αMHC-Angptl2 Tg mice and wild-type control mice. FIG. 4a shows the percent fractional shortening of cardiomyocytes isolated from αMHC-Angptl2 Tg mice (n=31, N=3) and wild-type control mice (n=40, N=3), FIG. 4b shows the mean Ca$^{2+}$ transients at 1 Hz stimulation, FIG. 4c shows the peak amplitude of Ca$^{2+}$ transients, FIG. 4d shows the time to peak [Ca$^{2+}$]i, and FIG. 4e shows the decay time constant T of Ca$^{2+}$ transients in cardiomyocytes from αMHC-Angptl2 Tg mice (n=54, N=3) and wild-type control mice (n=35, N=3). FIG. 4f shows the mean SR Ca$^+$ content in cardiomyocytes from αMHC-Angptl2 Tg mice (n=54, N=3) and wild-type mice (n=35, N=3). Data are expressed as the mean±SEM. *: $p<0.05$, **: $p<0.01$. N is the number of independent experiments.

FIG. 5 shows the results of Masson's Trichrome stain of the heart tissue sections from αMHC-Angptl2 Tg mice and wild-type mice 3 weeks after TAC treatment (scale bar: 100 μm).

FIG. 14 shows the prediction of the binding site of miR-135a, miR-204, miR-211, miR-221 and miR-222 in the mouse Angptl2 3'UTR in the FLuc-Angptl2-3'UTR construct. It shows the relative luciferase activity in NRCMs harboring FLuc-Angptl2-3'UTR construct and transfected with control pcDNA3.1 vector or miR-221, miR-222, miR-211, miR-204 or miR-135a expression vectors. Values from NRCMs transfected with the control pcDNA3.1 vector were set to 1. n=10-12 in each group. Data are expressed as the mean±SEM. *: p<0.05, **: p<0.01.

FIG. 15a is a schematic showing FLuc-Angptl2-3'UTR construct with (above) or lacking (below) the miR-221/222 binding site. The graph of FIG. 15a shows the relative luciferase activity in NRCMs harboring WT or deleted FLuc-Angptl2-3'UTR constructs and transfected with control or miR-221 or miR-222-expressing vectors. Values from NRCMs transfected with control pcDNA3.1 vector were set to 1. n=10-12 in each group. FIG. 15b shows the results of Western blot (left figure) and quantification (right figure) of ANGPTL2 in the heart of control or miR-221/222 KO mice after chronic exercise training. Hsc70 was served as a loading control. Levels in miR-221/222 non-KO control mice in the sedentary group were set to 1. Data are expressed as the mean±SEM. *: p<0.05, **: p<0.01.

FIG. 17a shows the results of measurement of PGC-1α and PPARα transcripts 2 weeks after administration of shRNA, and FIG. 17b shows the results of measurement of AKT and SERCA2a protein levels.

FIG. 18 shows the results of immunoblotting of ANGPTL2 in TAC-induced hypertrophic heart, without virus (control) or 4 weeks after intravenous administration of AAV6-shAngptl2-B at $1\times10^{10}$ vg/mouse or $3\times10^{10}$ vg/mouse. Hsc70 was served as a loading control. Data are expressed as the mean±SEM. *: p<0.05, **: p<0.01.

FIG. 19a to FIG. 19c shows the results of comparison of the indicated parameters among mice, without virus (control) or having received intravenous administration of AAV6-shAngptl2-B at $1\times10^{10}$ vg/mouse or $3\times10^{10}$ vg/mouse. Data are expressed as the mean±SEM. *: p<0.05, **: p<0.01.

FIG. 22a to FIG. 22c shows the results of confirming expression of ANGPTL2, AKT and SERCA2A in human iPS-derived cardiomyocytes transfected with siRNA targeting ANGPTL2 (siANGPTL2-B: s23854) or control siRNA. FIG. 22a shows the results of measuring the ANGPTL2 protein levels in the medium. n=4 in each group. FIG. 22b shows the results of Western blot of ANGPTL2, AKT and SERCA2A (left figure) and the relative protein level of AKT and SERCA2A. The experiment was conducted at least three times. Hsc70 was served as a loading control. Values from control siRNA were set to 1. FIG. 22c shows the results of expression of energy-related genes, PGC-1α and PPARα. Values from control siRNA were set to 1. Data are expressed as the mean±SEM. *: p<0.05, **: p<0.01, +: p<0.001.

FIG. 24 shows the positions of the sequences of siRNA targeting human ANGPTL2 used in the examples on the human ANGPTL2 sequence (SEQ ID NO. 1). The part surrounded by the line indicates the translated region.

DESCRIPTION OF EMBODIMENT

Figure 1:
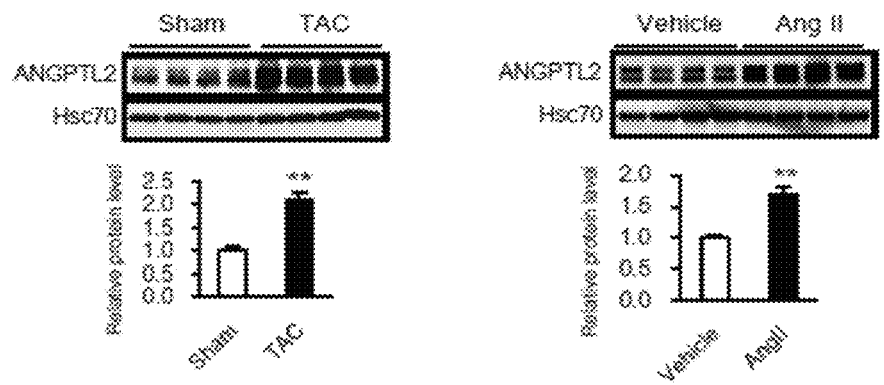
FIG. 1: The left figure shows the results of quantitating the expression of ANGPTL2 protein in the heart using Western blot 6 weeks after the TAC treatment of wild-type mice. Sham represents the sham control mouse. The graph shows the mean of each group (n=5). The right figure shows the results of quantitating the expression of ANGPTL2 protein in the heart of angiotensin II (Ang II)-induced pathological hypertrophy mouse model using Western blot 2 weeks after the induction. Vehicle shows the control mouse. The graph shows the mean of each group (n=8). Values from control were set to 1. Data are expressed as the mean±SEM. **: $p<0.01$.

Hereinafter, the present invention will be illustrated and described in detail with reference to the exemplary embodiments, along with the preferred methods and materials which can be used in practice of the present invention.

Unless otherwise specified in the sentences, any technical terms and scientific terms used in the present specification, have the same meaning as those generally understood by those of ordinary skill in the art to which the present invention belongs. Further any materials and methods equivalent or similar to those described in the present specification can be used for practicing the present invention.

Furthermore, all publications and patents cited herein in connection with the present invention described herein are incorporated herein by reference, for example, as indicating methodology, materials, etc. that can be used in the present invention.

Angiopoietin-like protein 2 (ANGPTL2) has been reported to be related to chronic inflammation associated with obesity, diabetes, atherosclerosis and progression of cancer.

The mRNA sequence of the human ANGPTL2 gene is shown in SEQ ID NO: 1.

According to the present invention, expression of the angiopoietin-like protein 2 gene in cardiomyocytes is suppressed. As a result, the present invention can prevent or delay the transition to heart failure and is effective for treatment or prevention of heart failure.

The present invention is characterized in that siRNA which is effective to degrade ANGPTL2 mRNA or its alternative splicing type RNA of a mammal (preferably, human) is used for suppressing expression of the ANGPTL2 gene in cardiomyocytes. The siRNA is a double-stranded RNA comprising a sense strand sequence having a sequence homologous to a partial sequence of ANGPTL2 mRNA or its alternative splicing type RNA of a mammal (preferably, human) and an antisense strand sequence as its complementary sequence. The number of nucleotides constituting each strand of sense and antisense sequences is about 18 to 29, preferably about 19 to 27, more preferably 19 to 25, further preferably 19 to 23. siRNA introduced into a cell or formed in a cell promotes the formation of an RNA-nuclease complex (RISC), thereby ANGPTL2 mRNA or its alternative splicing type RNA of a mammal (preferably, human) is selectively degraded and expression of ANGPTL2 is inhibited or suppressed.

Accordingly, the siRNA of the present invention contains a sense strand sequence of about 18 to 29 consecutive nucleotides from ANGPTL2 mRNA or its alternative splicing type RNA sequence of a mammal (preferably, human) and an antisense strand sequence as its complementary sequence.

As used herein, "alternative splicing type RNA" refers to mRNA that is generated as a result of cleavage at a site different from a normal splice site when mRNA precursor formed by transcription is spliced into mature mRNA.

Hereinafter, human ANGPTL2 will be described as a representative example, but the pharmaceutical composition and the method of the present invention can be used for treatment or prevention of heart failure in mammals.

According to an embodiment of the present invention, human ANGPTL2 mRNA is an RNA sequence coded by the nucleic acid sequence shown in SEQ ID NO: 1. The RNA sequence corresponds to a sequence in which all T in the nucleic acid sequence of SEQ ID NO: 1 has been replaced by U. From this RNA or the nucleic acid sequence, the siRNA sequence usable in the present invention can be determined. A target site on the mRNA for the siRNA to be used in the present invention can be selected using known knowledge. For example, descriptions of literatures such as U. Tei K., et al. Nucleic Acids Research (2004) 32 (3): 936-948, and the like, can be referred to, without limited to them. Further, criteria such as (i) the GC content is about 30 to about 70%, preferably about 50%, (ii) all bases are equal and G is not continuous, (iii) the base at the 5' end of the antisense strand is A or U, and the like, can be referred to, without limited to them. In examples of the present invention, the target site was selected by the criteria in that it is composed of 19 nucleotides following AA in which G and C are present after AA, without limited to this.

The feature which the siRNA used in the present invention should have is that when the siRNA is transfected into an animal cell (for example, a human cell), expression of the ANGPTL2 gene in the cell can be suppressed and a silencing effect on the ANGPTL2 gene can be generated. As used herein, "expression of the ANGPTL2 gene is suppressed and a silencing effect on the ANGPTL2 gene is generated" means "the effect of causing a decrease of ANGPTL2 at the protein level is generated". Accordingly, the siRNA used in the present invention is characterized by containing a target sequence which causes a decrease of ANGPTL2 at the protein level.

Further, it is desirable that expression of the ANGPTL2 gene as a target gene can be suppressed efficiently, and at the same time, high selectivity not affecting expression of unrelated genes (off-target effect) is attained, and the oligo nucleic acid (siRNA) itself does not express undesirable toxicity and side effects. Such siRNA sequence can be determined by those skilled in the art based on public knowledge and the siRNA itself can be obtained by those skilled in the art by preparing according to an ordinary method and investigating (for example, siRNA is actually prepared, transfected into cells, and activity of suppressing expression of the ANGPTL2 gene and toxicity on the cell are confirmed). No off-target effect can be confirmed, for example, by confirming that the cross-reaction does not occur for the candidate siRNA by utilizing a gene tip in advance, but the means is not limited to this.

The sense strand sequence of the siRNA sequence that can be used in the present invention preferably includes, for example, but not limited to, sequences of SEQ ID NOs: 2 to 8 shown below.

SEQ ID NO. 2:
GGAACAUUGACGGCGAAUA

SEQ ID NO. 3:
GAGAGUUCAUUUACCUAAA

SEQ ID NO. 4:
GGCUCUUACUCACUCAAGA

SEQ ID NO. 5:
GGCAUUGUGAGCGAGGUGA

SEQ ID NO. 6:
GCCAUUACCGGAGCCGCUA

SEQ ID NO. 7:
GUUUCCGCCUGGAACCUGA

SEQ ID NO. 8:
GAAACUGUGCCCACUACCA.

In addition, siRNAs containing as the sense strand sequence a sequence obtained by substitution, deletion or addition of one base in these sequences can also be used likewise as long as it has a silencing effect on the ANGPTL2 gene and it does not have the off-target effect which should be avoided. Substitution, deletion or addition of any one base in these sequences can be carried out according to an ordinary method. Also, it is possible, by using sequences designed as described above, to confirm whether siRNA prepared from these sequences generates the intended effect of the present invention, according to methods shown in examples of the present specification. Accordingly, sequences obtained by substitution, deletion or addition of one base in the above-described sequence are also included in the present invention provided that the effect of the present invention is obtained, and a pharmaceutical composition containing them and a method utilizing the same are also included in the present invention.

Moreover, a DNA sequence encoding RNA containing these sense strand sequences can also be used in the present invention, and is included in the present invention.

Furthermore, the sense strand sequence of the siRNA sequence which can be used in the present invention includes also the sequence of consecutive 18 to 29 nucleotides, preferably 19 to 27 nucleotides, more preferably 19 to 25 nucleotides, further preferably 19 to 23 nucleotides from ANGPTL2 mRNA or its alternative splicing type RNA, determined so as to include the main portion of any of the above-described sequences (for example, consecutive 12 or more, preferably 15 or more sequences in the above-described sequence). It is possible, by using sequences determined as described above, to confirm whether siRNA prepared from these sequences generates the intended effect of the present invention, according to methods shown in examples of the present specification. Accordingly, sequences determined so as to include the main portion of any of the above-described sequences are also included in the present invention provided that the siRNA prepared from them generates the effect of the present invention, and a pharmaceutical composition containing them and a method utilizing the same are also included in the present invention.

Moreover, a DNA sequence encoding RNA containing these sense strand sequences can also be used in the present invention, and is included in the present invention.

It is preferable that the siRNA used in the present invention has an overhang at the end of the sense strand sequence and/or the antisense strand sequence. The overhang of the siRNA is present at the 5' or 3' end, preferably at the 3' end of RNA. The number of nucleotides constituting the overhang is about 1 to 5, preferably about 1 to 4, more preferably about 2 to 3, further preferably 2. It is preferable that the overhang is T or U, or G. siRNAs having TT, UU or UG as the overhang are preferable, but the example is not limited to them.

As examples of the siRNA used in the present invention, those commercially available can also be used. Examples thereof include Angptl2 siRNA (catalog #sc-72351) marketed by Santa Cruz Biotech (USA), Angptl2 siRNA (catalog #SR415901) marketed by ORIGENE (USA), and Angptl2 siRNA listed in the Mission® siRNA library available from Sigma-Aldrich.

The siRNA used in the present invention may be a single siRNA or a mixture of a plurality of siRNAs (so-called cocktail). Each of the commercially available Angptl2 siRNAs described above is a mixture of a plurality of (3 to 5 kinds of) siRNAs.

When the siRNA of the present invention is used in vivo, the siRNA can be injected directly into the affected area, or a vector capable of expressing siRNA can be used.

When siRNA is injected directly into the affected area, it can be combined with liposomes, for example, lipofectamine, lipofectin, cellfectin and other positively charged liposomes and the formed composite can be injected.

When a vector capable of expressing the siRNA of the present invention is used, for example, an expression vector containing a DNA sequence encoding RNA containing a sense strand sequence and an antisense strand sequence as its complementary sequence of siRNA under control of a promoter is preferably used.

In order to obtain the siRNA of the present invention, hairpin type RNA can be used or hairpin type RNA can be expressed intracellularly.

The hairpin type RNA usable in the present invention contains the above-described sense strand sequence, the above-described antisense strand sequence and a single strand loop sequence bonding the above-described sense strand sequence and the above-described antisense strand sequence via covalent bond, and is processed by Dicer, an intracellular RNase, to form siRNA.

In the hairpin type DNA encoding the hairpin type RNA generating the siRNA of the present invention, a poly T sequence composed of 1 to 6, preferably 1 to 5 Ts, for example, TTTT or TTTTT composed of 4 or 5 Ts is connected to its 3' end, as the transcription termination signal sequence or for the overhang. In short hairpin RNA (shRNA) as the siRNA precursor transcribed from vector DNA, it is desirable that the 3' end of its antisense strand has an overhang composed of 2 to 4 Us, and because of the presence of the overhang, sense RNA and antisense RNA can get increased stability against digestion by nucleases. There is one endogenous Dicer in humans, which has a role of converting long-chain dsRNA and precursor microRNA (miRNA) into siRNA and mature miRNA, respectively. The above-described loop sequence in the present invention (indicating DNA sequence encoding RNA) includes, but not limited to, for example, TAGTGCTCCTGGTTG (SEQ ID NO: 16) and CAACCAGGAGCACTA (SEQ ID NO: 17), and known loop sequences can also be used.

Another exemplary DNA generating (encoding) the siRNA of the present invention is tandem type DNA, and this contains a DNA sequence encoding the above-described sense strand and a DNA sequence encoding the above-described antisense strand continuously in the 5'→3' direction, and is composed of a sequence in which a promoter is connected to the 5' end of each chain and a poly T sequence is connected to the 3' end of each chain, respectively. After intracellular transcription, sense RNA and antisense RNA generated simultaneously are hybridized to form siRNA.

Similarly to the above, the poly T sequence is preferably composed of 1 to 5, especially 4 to 5 Ts as the transcription termination signal sequence. Similarly to the hairpin type, the generated siRNA may have an overhang composed of 2 to 4 Us at the 3' end of the sense strand and/or antisense strand.

RNA or DNA having the RNA sequence or the DNA sequence of the present invention can be synthesized chemically or gene-recombinantly by well-known methods, but it is easy to synthesize it chemically using a conventional DNA/RNA automatic synthesizer in view of the number of nucleotides. It is also possible to prepare it by requesting synthesis to a siRNA-related custom synthesis company.

DNA having the DNA sequence of the present invention is incorporated into a vector and transcribed into RNA under control of a suitable promoter. The vector used in the present invention includes plasmids and viral vectors.

The promoter is not particularly restricted, and polIII promoters, for example, human or mouse U6 promoter and H1 promoter can be used.

It is preferable that siRNA has an overhang at the 5' or 3' end, preferably at the 3' end of RNA. Therefore, it is preferable that the DNA sequence encoding siRNA contains a sequence so constituted as to make an overhang. The number of nucleotides of the overhang is about 1 to 5, preferably about 1 to 4, more preferably about 2 to 3, further preferably 2. It is preferable that the overhang of siRNA to be coded is U or G. DNA sequences encoding UU and UG as the overhang of siRNA are preferable, but the example is not limited to them.

Plasmid vectors can be designed based on known reports. They can also be prepared by using commercially available vectors according to manufacturer's procedures. Furthermore, vectors designed to express the siRNA2 for Angptl2 are also commercially available, and can be used without limitations. Examples thereof include Angptl2 shRNA plasmid (catalog #sc-72351-SH) marketed by Santa Cruz Biotech (USA) and Retrovirus plasmid having Angptl2 shRNA (Cat #TG 502578) marketed by ORIGENE (USA).

The shRNA used in the present invention may be a single shRNA or a mixture of a plurality of shRNAs (so-called cocktail). Each of the commercially available Angptl2 shRNAs mentioned above is a mixture of a plurality of (3 to 5 kinds of) shRNAs. Further, in examples of the present specification, two shRNAs: AAV6-shAngptl2-B or AAV6-shAngptl2-A, are used separately, but they may be combined.

The plasmid vector usable in the present invention can contain drug resistant genes (e.g., puromycin resistant gene, hygromycin resistant gene), transcription termination sequences, unique restriction sites or multiple cloning sites, replication initiation points, Shine-Dalgarno sequences and the like, in general, in addition to the DNA sequence encoding the siRNA of the present invention and the promoter.

The plasmid vector can be complexed with a liposome selected from, for example, lipofectamine, lipofectin, cellfectin and other positively charged liposomes and capsulated and can be injected directly to the affected area. In gene introduction with the positively charged liposome, DNA is endocytosed into a cell, then, endosome and nuclear membrane are fused and the vector moves into the nucleus.

The viral vector usable in the present invention is not particularly limited and includes, for example, an adenoviral vector, an adeno-associated viral vector, a lentiviral vector, a retroviral vector (leukemia viral vector, etc.), a herpes viral vector and the like. As the viral vector, for example, those lacking in autonomous replication ability are preferable for preventing the onset of diseases when used in humans. For example, in the case of the adenoviral vector, autonomous replication defective adenoviral vectors lacking the E1 gene and the E3 gene can be used. The viral vector can be constructed according to known methods.

In the present invention, the adeno-associated viral vector having delivery selectivity into myocardium is particularly preferably used since it is intended to suppress expression of the ANGPTL2 gene in cardiomyocytes. As the adeno-associated viral vector, Type I to Type XI are known until now, and these can be used without restriction, but also vectors to be developed in the future can be used without restriction as long as the purpose of the present invention can be attained. The preferable vectors include, but not limited to, AAV1, AAV2, AAV3, AAV4, AAV5, AAV6 and AAV9, and particularly preferred is AAV6. Various adeno-associated viral vectors suitably used are commercially available.

In the case of using the viral vector, the vector can be directly injected into the affected area to infect the cell, thereby introducing genes into the cell. In particular, it has been confirmed that adenoviral vectors are capable of introducing genes into various cell types with very high efficiency, and they are actually clinically applied for gene therapy. Since this vector is not integrated into the genome, its effect is transient and safety is considered to be higher than other viral vectors.

The administration amount of the viral vector containing DNA encoding the sequence of siRNA contained in the pharmaceutical composition of the present invention is not particularly restricted and is $1.0 \times 10^{10}$ to $1.0 \times 10^{15}$, preferably $5.0 \times 10^{10}$ to $1.0 \times 10^{14}$, more preferably $1.0 \times 10^{11}$ to $1 \times 10^{11}$, further preferably $1.4 \times 10^{11}$ to $3 \times 10^{12}$ vg/injection. For example, when the adeno-associated viral vector (AAV) is used, the particularly preferable administration amount is $1.4 \times 10^{11}$ to $3 \times 10^{12}$ vg/injection. When directly administering siRNA or shRNA, the administration amount is not particularly limited, and an amount that generates the effect of causing a decrease in ANGPTL2 at the protein level is selected. The administration amount is the therapeutically effective amount and it can also be administered multiple times at regular time intervals. When actually used, the administration amount is determined according to the judgment of a medical specialist according to the patient's condition, age, sex, severity and the like.

The vector of the present invention is administered to a patient together with pharmaceutically acceptable carriers, for example, physiological saline solution, buffer solution and the like. The pharmaceutical composition may further contain a stabilizer, a preservative, an isotonicifier and the like. The method for administering the pharmaceutical composition of the present invention is not particularly limited, but either local administration or systemic administration can be carried out, and preferable is local administration. In the case of local administration, the affected part can be exposed under an endoscope such as a bronchoscope or the like or by surgical operation and the vector can be directly administered by means such as a syringe and the like. In the case of systemic administration, for example, the vector can be administered intravenously. As the dosage form, for example, a viral vector, or a complex of plasmid and liposome, is administered in a form suspended in a pharmaceutically acceptable carrier.

The present invention is also a method for determining whether a subject is suitable for treatment or prevention of heart failure with the pharmaceutical composition of the present invention by measuring the expression amount of angiopoietin-like protein 2 (ANGPTL2) in blood derived from a mammal (preferably, human).

Expression of angiopoietin-like protein 2 (ANGPTL2) can be measured based on an ordinary method, and for example, can be measured using an anti-ANGPTL2 antibody, but the method is not limited to this. The measurement method using an antibody includes, but not limited to, for example, immunological Western blot and an ELIZA method.

As the mammal from which blood is derived, humans are preferred, and blood derived from heart failure patients is particularly preferred for the purpose of determining whether they are suitable for treatment or prevention of heart failure with the pharmaceutical composition of the present invention.

The blood is preferably blood that sensitively reflects the amount of protein secreted from cardiomyocytes, and blood circulating through the heart, particularly, through the left ventricle is mentioned. Blood derived from the aortic base (Ao) and blood derived from the coronary sinus (CS) are particularly preferable, but the blood is not limited to them.

In the method of the present invention, when the expression level of ANGPTL2 in blood of the vein circulating through cardiac tissue, for example, the coronary sinus (CS) is higher than the expression level in blood of the artery directly before circulating through cardiac tissue, for example, the aortic root (Ao), it can be determined that the subject from which the blood is derived is in need of treatment or prevention of heart failure with the pharmaceutical composition of the present invention.

Alternatively, in the method of the present invention, when the expression level of ANGPTL2 in blood of the vein circulating through cardiac tissue, for example, the coronary sinus (CS) is higher than the previously-determined numerical value, it can also be determined that the subject from which the blood is derived is in need of treatment or prevention of heart failure with the pharmaceutical composition of the present invention.

In the method of the present invention, when it is determined that the subject is in need of treatment or prevention of heart failure with the pharmaceutical composition of the present invention as described above, the subject is judged to be a subject to which the pharmaceutical composition of the present invention is to be administered.

The method of the present invention is also a method for determining whether the therapeutic or preventive effect of heart failure is obtained in a subject by measuring expression of ANGPTL2 in blood derived from the subject to which a medicine, for example, the pharmaceutical composition of the present invention has been administered. For example, when the expression level of ANGPTL2 in blood of the vein circulating through cardiac tissue, for example, the coronary sinus (CS) is reduced after administering the pharmaceutical composition of the present invention, it can be determined that the therapeutic or preventive effect of the medicine is obtained.

Hence, the method of the present invention is also a method for determining whether the therapeutic or preventive effect of a medicine is obtained by measuring the concentration of ANGPTL2 in blood before and after administration of the medicine for treatment or prevention of heart failure.

The present invention is also a method for determining whether a subject is suffering from heart failure or at risk of developing heart failure by measuring expression of angiopoietin-like protein 2 (ANGPTL2) in blood from a mammal (preferably, human).

The method for measuring expression of angiopoietin-like protein 2 (ANGPTL2) is as described above.

Also for the mammal from which blood is derived, the site from which the subject blood is collected, and the like, the descriptions of the above-described determining method can be applied as they are.

The following facts have been found by the present inventors, indicating that the present invention can be a novel therapeutic or preventive medicine of heart failure.

1) ANGPTL2 production is activated in the heart of mice undergoing pathological remodeling and is potentially activated in some of the potential DCM patients.

2) Pathological stimulation increases production of ANGPTL2 in cardiomyocyte via calcineurin NFAT signaling.

3) ANGPTL2 activity (overexpression) in mouse heart accelerates development of heart failure (HF) by disrupting AKT-SERCA2a signaling and myocardial energy metabolism. On the other hand, Angptl2 knockout mice show increased AKT-SERCA2a signaling, amplified myocardial energy metabolism and ATP production, and non-pathological myocardial hypertrophy which is a phenotype similar to exercise-induced hypertrophy.

4) Exercise training and/or miR-221/222 activity reduces cardiac ANGPTL2 expression.

5) Angptl2 KO mice show increased AKT-SERCA2a signaling, amplified myocardial energy metabolism and ATP production, and are protected from pathological cardiac remodeling, and the phenotype of the heart of KO mice is similar to that induced by exercise.

6) Suppression of ANGPTL2 in the pathological hypertrophic condition of the heart activates AKT-SERCA2a signaling, enhances myocardial energy metabolism and blocks development of HF, in mice.

7) Activation of AKT-SERCA2a and enhanced myocardial energy metabolism occur in ANGPTL2 knockdown human iPS-derived cardiomyocytes.

From these facts, it was shown that cardiac ANGPTL2 activity dominates whether cardiac remodeling becomes pathological. In cardiopathology, it was shown that suppression of ANGPTL2 can repeat cardioprotective effect by exercise.

Calcineurin NFAT signaling increases expression of genes that promote pathological cardiac hypertrophy. The present inventors have shown that calcineurin NFAT signaling increases myocardial ANGPTL2 expression and ANGPTL2 activity exacerbates pathological cardiac remodeling. Interestingly, recent articles demonstrate that cardiac miR-222 expression increases after endurance exercise training, activity is required for physiological growth of cardiomyocytes in adult heart, and miR-222 expression protects against (harmful) cardiac remodeling. It is reported that miR-221 and miR-222 target the same sequence, and miR-221/222 improves pathological cardiac remodeling induced by pressure load (Peters, T. et al. Cardiovasc Res Suppl 103, S9-S46 (2014).).

The experimental results of the present inventors suggest that ANGPTL2 is the target of miR-221/222, and suppression of ANGPTL2 is the basis for cardioprotection mediated by miR-221/222. After exercise, the circulating miR-222 level is elevated in healthy individuals, ANGPTL2 and miR-221/222 binding site is fully conserved in human and mice, indicating that the functionality is preserved. These findings are consistent with the observation that ANGPTL2 is the direct target of miR-221 in hepatocellular carcinoma, and also consistent with the finding of the present inventors that ANGPTL2 is the direct target of miR-221 in chronic kidney disease (Morinaga et al., Kidney Int. 89: 327-341, 2016).

It is reported that as cardiac hypertrophy develops, mismatch occurs between the capillary number and the magnitude of cardiomyocytes, which leads to hypoxia of the myocardium. First, cardiac angiogenesis induced in the early stage of adaptation initially maintains cardiac function, but it becomes insufficient in the maladapted stage. This is probably due to reduced expression of vascular endothelial growth factor (VEGF). Therefore, the reduced myocardial oxygen level probably regulates the development of HF. Anti-VEGF therapy has been reported to increase ANGPTL2 expression in return for attenuating VEGF signaling in tumor cells. ANGPTL2, like VEGF, has angiogenesis promoting activity in the tumor microenvironment. Therefore, increased ANGPTL2 expression possibly occurs in hypertrophic hearts due to hypoxia caused by the deficiency of VEGF. Furthermore, the increase in ANGPTL2 seen in pathological remodeling environment probably exacerbates cardiac dysfunction by decrease of the ejection fraction due to attenuated AKT-SERCA2a signaling and reduced myocardial energy metabolism. Recent papers suggest that upregulated VEGF and VEGF receptor mRNA levels are observed after exercise training, suggesting cardiac capillary angiogenesis. This environment is related to improvement of aging-related capillaries and deficient blood supply. Observation of decrease in Angptl2 mRNA level in mice after endurance exercise training suggests that exercise controls transcription of Angptl2. With mouse aging, an increase in ANGPTL2 production in the heart was observed. Therefore, in the case of exercise-induced hypertrophy, maintaining the proper myocardial oxygen level downregulates expression of ANGPTL2, and the capillary number and the magnitude of cardiomyocyte can be normally controlled by VEGF.

Recent articles show that mice receiving exercise training are protected from pathologic cardiac hypertrophy, reduced systolic function, and pulmonary congestion, and activation of PI3K-Akt signaling is necessary for exercise-induced cardioprotection. In previous studies, Tg mice overexpressing Akt in cardiomyocytes showed cardiac hypertrophy with enhanced left ventricular function associated with increased expression of SERCA2a. Protection from pathological cardiac remodeling by activation of AKT-SERCA2a was also observed in Angptl2 KO mice in the following examples. This suggests that suppression of ANGPTL2 is the basis of exercise-induced cardioprotection. These findings also suggest that upregulated ANGPTL2 antagonizes AKT activation. The following results support the idea that SERCA2a maintains the ability of the heart by controlling the homeostasis of $Ca^{2+}$ in cells in functional cardiomyocytes by myocardial contraction and relaxation. Since the activity of SERCA2a is changing with the pathological condition of the heart, restoring its normal activity is proposed as a strategy for managing cardiac dysfunction. CUPID phase 1 trial of gene therapy (AAV1/SERCA2a) in HF patients supports this approach, but phase 2b trial did not satisfy primary and secondary end points. This suggests that restoration of SERCA2a alone is not enough to improve HF.

Optimization of myocardial energy metabolism necessary for proper ATP production is considered important for treating HFrEF and HFpEF. Transcript levels of PPARα and PGC-1α are decreasing in pathologic hypertrophy and genes governing mitochondrial biogenesis and β-oxidation are regulated by PPARα and PGC-1α. Higher abundance of both factors allows cardiac cells to depend on lipid oxidation for energy production. The present inventors showed that suppression of cardiac ANGPTL2 markedly increased the mRNA levels of PPARα and PGC-1α and this event is related to intracellular ATP production. As reported elsewhere, AKT signaling appears to increase transcript levels of PPARα and PGC-1α. In summary, it is suggested that inactivation of ANGPTL2 may restore cardiac function and energy metabolism in relation to pathological hypertrophy.

Interestingly, ANGPTL2 production in the heart occurred in nearly 40% of DCM patients studied. This suggests that cardiac dysfunction is exacerbated by ANGPTL2 activity and that a panel of these patients may be candidates for therapeutic ANGPTL2 suppression. These findings also suggest that mechanism underlying diseases such as DCM differ between individuals, and approach of personalized medicine is necessary in the treatment of these diseases. DCM patients with apparently active production of ANGPTL2 were older than other DCM patients. Activation of cardiac ANGPTL2 may be associated with age-related dysfunction, since dysfunction is common in senescent hearts and expression of ANGPTL2 is associated with the senescence-associated secretory phenotype (SASP).

Mice injected intravenously with AAV6 vector expressing shRNA of Angptl2 had lower severity regarding cardiac hypertrophy induced by TAC, as compared to mice not administered. Higher doses of shRNA were more effective against cardiac dysfunction than lower doses. This suggests that the effectiveness of AAV6 gene introduction depends on the dose. The dosage of AAV6 used in this example is lower than that reported to be appropriate. Therefore, administration of higher doses of AAV6-shAngptl2-B than used in this example would be able to more effectively protect the heart. Other factors affecting AAV transduction to the heart, for example, selection of a preferential serotypes to the heart, or delivery approach other than intravenous injection is useful for further clinical application. In interpreting the above-described CUPID gene therapy trial, researchers say that less effect than expected may be ascribable to low gene introduction. In contrast, gene therapy targeting ANGPTL2 has a merit that by comparing the ANGPTL2 concentration of the aortic root and the coronary sinus, gene transfer efficiency can be easily monitored.

In summary, the present inventors have found that the transition from adapted to maladapted cardiac remodeling is accelerated by ANGPTL2 activity induced by pathologic cardiac stimulation, and suppression of ANGPTL2 can restore cardiac function and myocardial energy metabolism and inhibit development to pathological remodeling. According to the present invention, a beneficial cardioprotective effect of exercise can be reproduced, and the present invention can also be applied to HF patients who can not participate in regular exercise.

EXAMPLES

Hereinafter, the present invention will be described in detail with reference to examples, but the present invention is not limited to the following.

I. Materials and Methods

1. Animal Studies

All experimental procedures were approved by the Kumamoto University Ethics Review Committee for Animal Experimentation. All animals were fed a normal diet, with automatically controlled lighting (12 hr on, 12 hr off), and maintained at 23° C. Genetically engineered mice used in the study were: Angptl2 knockout mice (Angptl2 KO1) on a C57BL/6NJcl background, transgenic (Tg) mice overexpressing Angptl2 driven by the aP2 promoter on a C57BL/6NJcl background ((aP2-Angptl21), Tg mice overexpressing EGFP driven by the murine αMHC promoter on a C57BL/6J background (αMHC-EGFP2), and Tg mice overexpressing Angptl2 in keratinocytes on a FVB/N background (K14-Angptl23). Angptl2 KO mice were maintained by heterozygous breeders. KK-Ay and db/db mice were purchased from CLEA Japan (Tokyo, Japan).

2-1. Generation of αMHC-Angptl2 Transgenic Mice cDNA encoding mouse Angptl2 was cloned into the αMHC promoter expression vector, kindly provided by Dr. Jeffrey Robbins of the Heart Institute of Cincinnati Children's Hospital Medical Center. To identify Tg offspring, genomic PCR was performed with the following forward and reverse primers: forward primer (5'-ACTTCTACAT-GAGATCATTC-3': SEQ ID No. 18) and reverse primer (5'-GGTATTCTCAGGCTTCACCAGGTA-3': SEQ ID No. 19). To maintain an isogenic strain, mice were propagated as heterozygotes by breeding with wild-type C57BL/6NJcl mice. Animals from F2 or F3 generations were used in all studies.

2-2. Generation of miR-221/222 conditional knockout mice miR-221/222 conditional knockout mice on a C57BL/6N background were provided by the German Research Center for Environmental Health (Germany). To maintain an isogenic strain, mice were propagated as heterozygotes by breeding with wild-type C57BL/6NJcl mice.

3. Establishment of Hypertrophy Mouse Models Induced by Transverse Aortic Constriction (TAC)

Male mice approximately 10 weeks old (body weight of 23-25 g) were subjected to pressure overload using TAC surgery. In brief, mice were anaesthetized by intraperitoneal injection of pentobarbital. The aortic arch was accessed via a left thoracotomy, and the thoracic aorta at the arch was surgically constricted using a 27-gauge needle to generate trans-stenotic pressure. Sham mice underwent the same procedure without aortic banding.

4. Angiotensin II Treatment

Angiotensin II (Ang II) was dissolved in 150 mM NaCl and 1 mM acetic acid. Ang II (3 mg/kg/day) was continuously infused into dorsal subcutaneous tissues of mice for 2 weeks using a mini-osmotic pump. Vehicle-treated groups underwent the same procedure with vehicle (150 mM NaCl and 1 mM acetic acid).

5. Isolation of Cardiomyocytes and Non-Cardiomyocytes

Ventricles were harvested from αMHC-EGFP transgenic mice (three hearts per sample), and tissue was minced into small pieces and digested by 0.075% collagenase, 0.12% trypsin and 0.02% DNase at 37° C. for 40 minutes. Cells were collected and resuspended and then passed through a 100 μm mesh filter into 50-ml centrifuge tubes. Cells were finally resuspended with 0.5 ml FACS buffer (phosphate-buffered saline (PBS)/0.1% BSA) and GFP-positive (cardiomyocyte) and GFP-negative (non-cardiomyocyte) cells were isolated using a cell sorter FACSAria II (Becton Dickinson, USA).

6. Histological Analysis

Mouse heart tissue samples were fixed in 4% paraformaldehyde for 24 hrs and embedded in paraffin. Blocks were cut into 4-μm-thick sections, air-dried, and deparaffinized. Sections were stained with hematoxylin and eosin (H&E) to evaluate morphology, wheat germ agglutinin (WGA), or Masson's Trichrome. Slides were mounted and examined using a BIOREVO BZ-9000 microscope (KEYENCE, Japan). Quantification of cardiomyocyte size after Alexa Fluor® 594-conjugated WGA and DAPI (4', 6 diamidio-2-phenylindole) staining was undertaken. In each ventricle, 100 cardiomyocytes were measured using BZ-H2A software (KEYENCE, Japan). Measurements were limited to cardiomyocytes cut perpendicular to their long axis at the level of a centered round cardiomyocyte nucleus. Quantification of fibrosis areas was undertaken by visualizing blue-stained areas. The fibrotic area was calculated using Image J software (National Institutes of Health) as the summation of blue-stained areas divided by total ventricular area.

7. Real-Time Quantitative RT-PCR Analysis

Total RNA was isolated using an RNeasy Mini Kit (Qiagen, USA). DNase-treated RNA was reverse transcribed using a PrimeScript RT reagent Kit (Takara Bio Inc, Japan). Heart tissue was homogenized using a Multi-beads Shocker®. Real-time quantitative RT-PCR was performed using SYBER Premix Ex Taq(trademark) II (Takara Bio Inc, Japan) and a Thermal Cycler Dice Real-Time system (Takara Bio Inc, Japan). Relative transcript abundance was normalized to that of 18S rRNA levels in mouse, rat, and human samples. Forward and reverse oligonucleotides of the genes below were used for RT-PCR.

Mouse: Rps18, Angptl2, BNP, Myh7, CTGF, Col1, Col3a, PGC-1α, PGC-1β, Nrf1, Nrf2, RXRα, PPARα, FATP, CD36, Fabp3, Acsl1, CPT1α, CTP1β, Acads, Acadm, Acox1, ND6, ND4, as9, Cyt.b, Cyt.c, Cox1, Cox2, Cox3, ATPase6, ATP5a1, ATP5b.

Rat: Rps18, Angptl2, ANP, BNP, MYH7, Serca2a, PGC-1α, PPARα.

After 24 hrs, media was changed prior to treatment with various reagents or adenovirus infection unless otherwise specified.

For ANGPTL2 knockdown in NRCMs, NRCMs were transfected with Mission siRNA Universal Negative Control (siControl; Sigma-Aldrich) or with three validated Mission siRNAs targeting Angptl2 (siAngptl2-A: SASI_Rn01_00093802: GGAUCUUACUCACUCAA-GATT (SEQ. ID. NO. 20), siAngptl2-B: SASI_Rn01_00093800: GAGAGUACAUUUACCU-CAATT (SEQ. ID. NO. 21), siAngptl2-C: SASI_Rn01_00093799: CCAGAAAGCGAGUAC-UAUATT (SEQ. ID. NO. 22), Sigma-Aldrich) using Lipofectamine® RNAiMAX reagent (Life technologies, USA) according to the manufacturer's instruction. 48 hr later, cells were treated with TRI Reagent® (Cosmo Bio, Japan) in preparation for real-time RT-PCR or harvested and lysed with lysis buffer for immunoblot analyses.

For constitutively active NFAT overexpression in NRCMs, NRCMs were electroporated with pcDNA3.1 as negative control or constitutively active mouse NFATc3 expression plasmid, kindly provided by Dr. Takashi Minami (Institute of Resource Development and Analysis, Kumamoto University, Japan), using Amaxa rat cardiomyocyte-neonatal nucleofector Kit® and Nucleofector Device® (Lonza, USA) according to the manufacturer's instruction. After electroporation, cells were plated and cultured for 24 hrs.

Production of recombinant adenovirus expressing Angptl2 (Ad-Angptl2) was conducted with Takara Bio Inc. (Japan). In brief, mouse Angptl2 cDNA was cloned into the Smi I site of the pAxCAwtit2 cosmid vector (Takara Bio Inc, Japan), which was used to transfect 293 cells. Recombinant adenoviruses expressing dominant-negative AKT (Ad-dnAKT) and LacZ (Ad-LacZ) were kindly provided by Dr. Takashi Kadowaki (Department of Metabolic Diseases, University of Tokyo, Japan). NRCMs were infected with adenovirus vectors 1 hr after seeding at a MOI of 50. Culture medium was then replaced with new medium, and cells were cultured for 48 hrs.

For Ang II and Isoproterenol (ISO; Sigma-Aldrich) treatment, NRCMs were stimulated with 100 nM Ang II or 100 nM ISO for 6 and 12 hrs. For cyclosporine A (CsA) treatments, NRCMs were pretreated with CsA for 30 minutes prior to treatment with Ang II and ISO.

For NFAT immunocytochemistry staining, NRCMs were plated on collagen-coated coverslips with or without 100 nM Ang II in serum-free medium. After 12 hrs, cells were rinsed with PBS, fixed with 4% paraformaldehyde in PBS for 5 min, and permeabilized with 0.4% Triton X-100 for 15 min. Nonspecific binding was minimized by blocking with 3% normal goat serum in PBS. Cells were incubated with anti-NFATC1 (sc-7294; SantaCruz Biotechnology, USA) or NFATC4 polyclonal antibodies (ab62613; Abcam, USA) at 1 µg/ml, followed by incubation with Alexa Fluor®488-conjugated anti-rabbit antibodies. Nuclei were counterstained with 4',6'-diamidino-2-phenylindole (DAPI). Images were obtained using a fluorescence microscope (model BZ-9000).

13. Endurance Exercise Training

Ten-week-old male C57BL/6NJcl mice were allowed to adapt to the treadmill chamber (Model MK-680AT/02M, Muromachi Co., Ltd, Japan) for 30 minutes with unlimited movement. Mice were then subjected to warm-up treadmill running for 15 minutes (at 5 m/min for 5 min, 10 m/min for 5 min, and 15 m/min for 5 min) before real endurance exercise training began. Mice began treadmill running at a 20 m/min for 60 min as an acute endurance exercise. For chronic endurance exercise, mice repeatedly performed a warm-up for 15 minutes and subsequent treadmill running at 20 m/min for 60 min 5 days per a week for 3 weeks. Mice were sacrificed 3 hrs after the last running exercise and heart tissue analyzed.

14. Luciferase Reporter Assays

To construct the reporter plasmid (FLuc-Angptl2-3'UTR), the 3'UTR of mouse Angptl2 was amplified from genomic DNA by polymerase chain reaction (PCR) and then cloned into a Xba I site downstream of the firefly luciferase (FLuc) gene in the pGL3-Promotor Vector (Promega, USA). To delete the miR-221/222 binding site from the Angptl2 3'UTR, the following primer set was designed: 5'-CATTTCTCATGTTCTGTGTATATATAAAAGGGAGG-3' (SEQ ID NO. 23) and 5'-AGAACATGAGAAATGCT-GAGGTAACAGGGCAG-3' (SEQ ID NO. 24). Deletion of the miR-221/222 binding site in the Angptl2-3'UTR reporter (Fluc-Angptl2-3'UTR-A221/222) was performed using a PrimeSTAR mutagenesis basal kit (Takara Bio Inc, Japan) according to the manufacturer's instruction. miR-221, miR-222, miR-211, miR-204 or miR-135a overexpression vectors were constructed by inserting sequences including the full-length mature microRNA sequences into pBApo-CMV (Takara Bio Inc, Japan). NRCMs were co-transfected with pcDNA3.1 as a negative control or plasmids encoding microRNA plus the phRL-TK vector (Promega, USA), which encodes renilla luciferase (RLuc) and either the FLuc-Angptl2-3'UTR or FLuc-Angptl2-3'UTR-A221/222 using Lipofectamine® 3000 reagent (Life technologies, USA). Luciferase activities were determined using a Dual Glo luciferase assay system (Promega, USA) according to the manufacturer's instruction.

15. Recombinant Adeno-Associated Virus (AAV) Treatment

Production and purification of recombinant AAV6 vectors were conducted with Takara Bio Inc (Japan). In brief, for shRNA synthesis, single-stranded DNA oligonucleotides A and B harboring mouse Angptl2-targeting siRNA and complementary strands were designed as follows:

```
A-top
                                    (SEQ ID NO. 25)
5'-CTAGAGAGAGTACATTTACCTCAATAGTGCTCCTGGTTGTTGAGGTA
AATGTACTCTCTTTTTTA-3'
and A-bottom
                                    (SEQ ID NO. 26)
5'-CTAGTAAAAAAGAGAGTACATTTACCTCAACAACCAGGAGCACTATT
GAGGTAAATGTACTCTCT-3';

B-top
                                    (SEQ ID NO. 27)
5'-CTAGAGCCAGAAAGCGAGTACTATATAGTGCTCCTGGTTGTATAGTA
CTCGCTTTCTGGCTTTTTTA-3'
and B-bottom
                                    (SEQ ID NO. 28)
5'-CTAGTAAAAAAGCCAGAAAGCGAGTACTATACAACCAGGAGCACTAT
ATAGTACTCGCTTTCTGGCT-3';

Scramble-top
                                    (SEQ ID NO. 37)
5'-CTAGAGTCTTAATCGCGTATAAGGCTAGTGCTCCTGGTTGGCCTTAT
ACGCGATTAAGACTTTTTTA-3';
and Scramble-bottom
                                    (SEQ ID NO. 38)
5'-CTAGTAAAAAAGTCTTAATCGCGTATAAGGCCAACCAGGAGCACTAG
CCTTATACGCGATTAAGACT-3'.
```

In each sequence above, mouse Angptl2 targeting sequence of the sense strand and antisense strand is underlined. The sequences TAGTGCTCCTGGTTG (SEQ ID NO. 16) and CAACCAGGAGCACTA (SEQ ID NO. 17) between the underlined sequences are loop sequence.

Single-stranded oligonucleotides (shAngptl2-A, shAngptl2-B, and shScramble) were annealed and cloned into the pAAV-2xU6 vector (Takara Bio Inc, Japan). Recombinant AAV6 vectors were produced with a AAVpro Helper Free System (Takara Bio Inc, Japan), purified by cesium chloride density gradient centrifugation, and dialyzed against PBS. The genome copy number was determined using an AAVpro Titration Kit (for Real-time PCR) Ver. 2 (Takara Bio Inc, Japan).

For analysis of TAC animals, 10-week-old male C57BL/6NJcl mice were subjected to TAC surgery and 2 weeks later anesthetized with 2% isoflurane and intravenously injected with recombinant AAV6 vectors at $1 \times 10^{10}$ vg or $3 \times 10^{10}$ vg. Cardiac function was examined using echocardiography before injection (2 weeks before TAC surgery), and at 2 weeks, and 4 or 5 weeks after injection. After echocardiography at 4 or 5 weeks, mice were sacrificed and heart tissues subjected to histological, real-time RT-PCR, and immunoblot analyses. In some experiments, 10-week-old male C57BL/6NJcl mice were intravenously injected with recombinant AAV6 vectors at $1 \times 10^{10}$ vg or $3 \times 10^{10}$ vg. Two weeks after injection, mice were sacrificed and heart tissues subjected to real-time RT-PCR and immunoblot analyses.

16. ANGPTL2 Knockdown in Human iPS-Derived Cardiomyocytes

Human iPS cell lines 253G4 or 836B3 served as pluripotent cells. Cardiomyocyte differentiation of both was induced as reported (Tohyama, S., et al., Cell Stem Cell 12, 127-137 (2013); Uosaki, H., et al., PLoS One 6, e23657 (2011); Hemmi, N., et al. Stem Cells Transl Med 3, 1473-1483 (2014)). Derived cardiomyocytes were transfected with Mission siRNA Universal Negative Control (Sigma-Aldrich) or human ANGPTL2 targeting siRNA (siANGPTL2-A: s23855: GGAACAUUGACGGCGAAUAUU (SEQ ID NO. 29); siANGPTL2-B: s23854: GAGAGUUCAUUUACCUAAAUU (SEQ ID NO. 30); siANGPTL2-C: s23853: GGCUCUUACUCACUCAAGAUU (SEQ ID NO. 31); siANGPTL2-D: SASI_Hs01_00042802: GGCAUUGUGAGCGAGGUGAUU (SEQ ID NO. 32); siANGPTL2-E: SASI_Hs01_00042803: GCCAUUACCGGAGCCGCUAUU (SEQ ID NO. 33); siANGPTL2-F: SASI_Hs01_00042804: GUUUCCGCCUGGAACCUGAUU (SEQ ID NO. 34); siANGPTL2-G: SASI_Hs01_00042806: GAAACUGUGCCCACUACCAUU (SEQ ID NO. 35)) with Lipofectamine® RNAi MAX reagent (Life technologies, USA) according to the manufacturer's instruction. siANGPTL2-A, B, and C were purchased from Life technologies, and siANGPTL2-D, E, F, and G were purchased from Sigma-Aldrich. The locations of each sequence in human ANGPTL2 sequence (SEQ ID NO. 1) are shown in FIG. 24. At 12 hrs after transfection, the medium was changed and cells were incubated for an additional 48 hrs. ANGPTL2 concentration in conditioned medium from transfected cells was estimated with an ANGPTL2 ELISA kit (IBL, Japan) according to the manufacturer's instructions. Cells were treated with TRI Reagent® for real-time RT-PCR analyses or harvested and lysed with RIPA (50 mM Tris-HCl, 150 mM NaCl, 0.5% sodium deoxycholate, 0.1% SDS, 1% Nonidet P-40, 1 mM EDTA, Protease inhibitor (Roche), pH 7.5) buffer for immunoblot analyses.

17. Human Studies

A total of 58 patients with dilated cardiomyopathy (DCM) (40 men and 18 women; mean age±SEM, 54.7±1.7 years) were enrolled in the study. Twenty-six were classified as New York Heart Association (NYHA) class I, 27 were class II, and 5 were class III. Individuals with an episode of acute HF within the previous 3 months or with renal dysfunction [estimated glomerular filtration rate (eGFR) of <30 mL/min/1.73 m$^2$] were excluded from the study. All subjects underwent coronary angiography to exclude the possibility of coronary artery disease and endomyocardial biopsy to exclude myocarditis or specific muscle disease. DCM was defined as the presence of both a left ventricular (LV) ejection fraction (EF) of <50% (as revealed by contrast left ventriculography) and a dilated LV cavity in the absence of coronary artery stenosis of >50%, valvular heart disease, arterial hypertension, and secondary cardiac muscle disease attributable to any known systemic condition. No patients had histories of acute viral myocarditis or familial DCM. There was also no evidence that immune triggers functioned in DCM development in any patient. Patients were in stable condition before their referral to a university hospital for cardiac catheterization. Written informed consent was obtained from each patient before cardiac catheterization, and the study was approved by the Human Ethics Committee of the Nagoya University School of Medicine, Japan (protocol approval No. 359-7, Mar. 16, 2015).

18. Cardiac Catheterization Analysis

All patients underwent diagnostic right and left heart catheterization as previously described (Okamoto, R., et al. Int Heart J 54, 202-206 (2013); Sakakibara, M., et al. Diabetes Res Clin Pract 92, 348-355 (2011)). In brief, pulmonary arterial wedge pressure (PCWP) and cardiac output (CO) were measured with the use of a Swan-Ganz catheter inserted through the right internal jugular vein. Cardiac index (CI) was calculated as follows: CI=CO/body surface area (L/min/m$^2$). Coronary angiography and left ventriculography via the right radial or femoral artery were also performed. A 6F fluid-filled pigtail catheter was positioned in the left ventricle for measurement of LV pressure. EF was assessed by left ventriculography using the area-length method. To examine transcardiac release of serum ANGPTL2, at the time of biventricular catheterization ANGPTL2 from the aortic root (Ao) and ANGPTL2 from the coronary sinus (CS) were collected simultaneously. Serum ANGPTL2 levels were determined with human ANGPTL2 ELISA kits (IBL, Japan).

19. Ultrasonic Echocardiographic Analysis of Human Patients

Two-dimensional echocardiography was performed using a ViVid 7 system (ViVid 7, GE Healthcare, USAA) as described (Okamoto, R., et al. Int Heart J 54, 202-206 (2013)). LV end-diastolic dimension (LVDd), LV end-systolic dimension (LVDs), and left arterial dimension (LAD) were measured. Percent fractional shortening (% FS) was calculated from LVDd and LVDs. The LV mass index (LVMI) was calculated from two-dimensional measurements according to a formula approved by the American Society of Echocardiology.

20. Immunohistological Analysis

Human heart tissue samples were obtained from patients, including from congestive heart failure (CHF) patients and non-CHF patients. In all cases, written informed consent was obtained from relevant families. The study was also approved by the Ethics Committees of Kumamoto University. Human heart tissue samples were fixed in 4% paraformaldehyde for 24 hrs and embedded in paraffin. Blocks were cut into 4-μm-thick sections, air-dried, and deparaffinized.

For immunohistochemistry, sections were pretreated with periodic acid to inhibit endogenous peroxidases. Subsequently, specimens were incubated overnight with 100-fold diluted rabbit polyclonal anti-human ANGPTL2 antibody produced by immunizing rabbits with a synthetic peptide corresponding to amino acids 383-400 (SFRLEPESEYYKLRLGRY: SEQ ID No. 36) of human ANGPTL2 at 4° C. After washing with PBS, specimens were incubated with 500-fold diluted goat anti-rabbit IgG conjugated with peroxidase as second antibody at room temperature for 60 min. Specimens were then counterstained with hematoxylin. As negative controls, the same procedures were performed using isotype control IgG rather than primary antibodies. Peroxidase activity was visualized by incubation with a 3,3-diaminobenzidine solution and analyzed by light microscopy (model BZ-9000). For double immunofluorescent staining, a rabbit polyclonal anti-human ANGPTL2 antibody (1:100) was used with goat polyclonal anti-human αMHC (1:100), mouse monoclonal anti-human CD31 (1:100) and goat polyclonal anti-human PERIOSTIN (1:100). Alexa Fluor® 488-conjugated anti-rabbit or Alexa Fluor® 594-conjugated anti-goat/mouse antibody served as second antibody. After washing with PBS, fluorescent images were captured by confocal laser microscopy (LSM410, Zeiss, Germany).

21. Statistical Analysis

All values were reported as the mean±SEM. Data were assessed with two-group comparisons of variables by unpaired two-tailed t-test. The Kaplan-Meier log-rank test was applied to analyze mouse survival data and calculated with GraphPad Prism software (version 5.0, GraphPad Software). A value of $p<0.05$ was considered statistically significant.

II. Experimental Results (Example 1) ANGPTL2 Expression Increases in Pathological Cardiac Hypertrophy in Mice To assess ANGPTL2 function in heart, ANGPTL2 protein levels was assayed in heart tissue in a mouse cardiac hypertrophy model induced by pressure overload using severe transverse aorta constriction (TAC) and compared to those in sham-operated controls. Mice were subjected to TAC surgery or sham surgery and 6 weeks later protein levels were measured by Western blotting. The results were shown in the left figures of FIG. 1. Higher ANGPTL2 protein levels were observed in heart tissues of TAC animals relative to those in sham-operated controls.

Mice undergoing TAC showed cardiac hypertrophy with left ventricular dilatation, decreased fractional shortening (FS), and increased expression of fetal cardiac genes (such as the heart failure markers ANP, BNP, and Myh7) and cardiac fibrosis markers (CTGF, Col1, and Col3a1) and developed HFrEF due to systolic dysfunction with left ventricular dilatation (Data not shown).

Moreover, ANGPTL2 protein levels in heart tissues of Angiotensin II (Ang II)-induced pathological hypertrophy mouse model is assessed. Two hrs after Ang II treatment or vehicle treatment as control ANGPTL2 protein levels were measured as above. The results were shown in the right figures of FIG. 1. ANGPTL2 protein levels in heart tissues were significantly increased in angiotensin II (Ang II)-induced pathological hypertrophy relative to vehicle-treated controls.

In this Ang II-induced model, mice showed no left ventricular dilatation and preserved fractional shortening (FS) but exhibited increased expression of ANP, BNP, Myh7, CTGF, Col1, and Col3a1, suggesting that Ang II-induced hypertrophy is a pathological cardiac remodeling event associated with HFpEF.

Figure 2A:
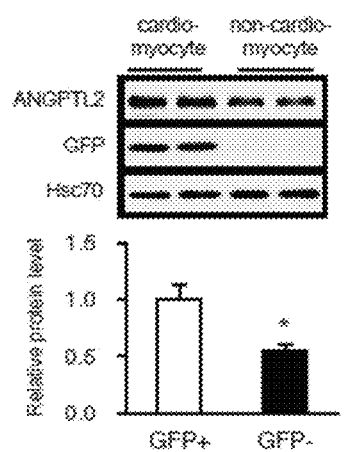
Figure 2A:
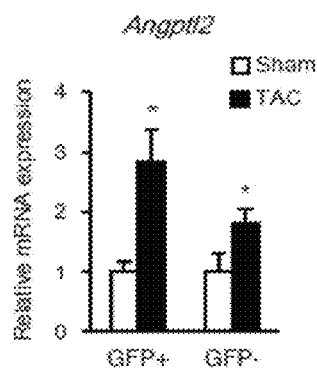
Figure 2A:
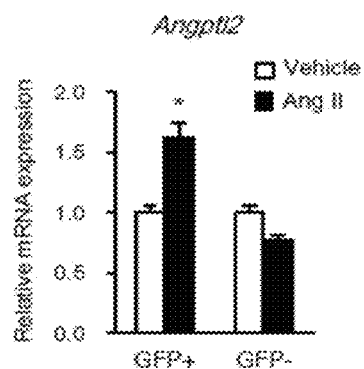

Then, cardiomyocytes and non-cardiomyocytes were collected separately from transgenic (Tg) mice expressing enhanced green fluorescent protein (EGFP) under control of the cardiomyocyte-specific promoter αMHC (αMHC-EGFP Tg mice), and subject to immunoblotting. The results are shown in FIG. 2(a). Immunoblotting revealed more abundant ANGPTL2 expression in GFP-positive cardiomyocytes than in GFP-negative cells. Moreover, RT-PCR analysis revealed increased Angptl2 expression in GFP-positive cardiomyocytes in both TAC and Ang II-induced hypertrophied heart, as shown in FIGS. 2(b) and (c). It suggests that increased ANGPTL2 expression in pathological remodeling occurs primarily in cardiomyocytes.

(Example 2) Cardiac Dysfunction of Mice Overexpressing ANGPTL2 in Cardiomyocytes It is examined whether increased ANGPTL2 proteins in heart promote pathological remodeling. To do so, four transgenic mouse lines overexpressing ANGPTL2 in cardiomyocytes under control of the αMHC promoter (αMHC-Angptl2 Tg mice) were generated. All appeared normal at birth, indicating that ANGPTL2 up-regulation does not grossly perturb cardiac development. Three lines (#1-9, #2-3, and #2-14) showed increased ANGPTL2 expression in heart similar to that seen in TAC-induced hypertrophy and were chosen for further analysis.

Figure 3A:
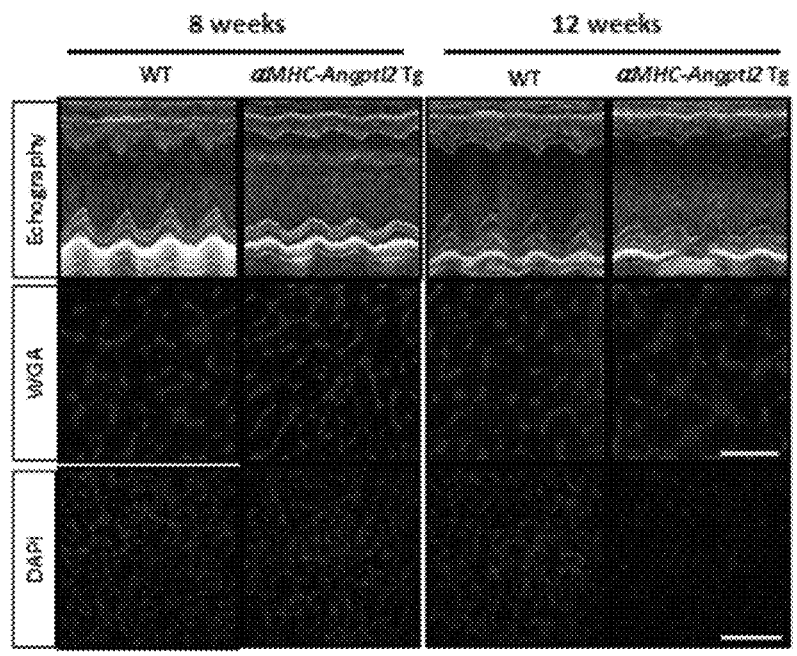
FIG. 3a shows the results of confirming cardiac contractile dysfunction of 8-week old and 12-week old αMHC-Angptl2 Tg mice and wild-type littermates. The upper part of FIG. 3a is the recording of M-mode ultrasound examination. The middle part of FIG. 3a is the result for the left ventricle sections stained with wheat germ agglutinin (WGA), which indicates the size of the cardiomyocyte (scale bar: 50 μm). The lower part of FIG. 3a is the result for the left ventricle sections stained with DAPI, which indicates the size of the cardiomyocyte (scale bar: 200 μm).
Figure 3B:
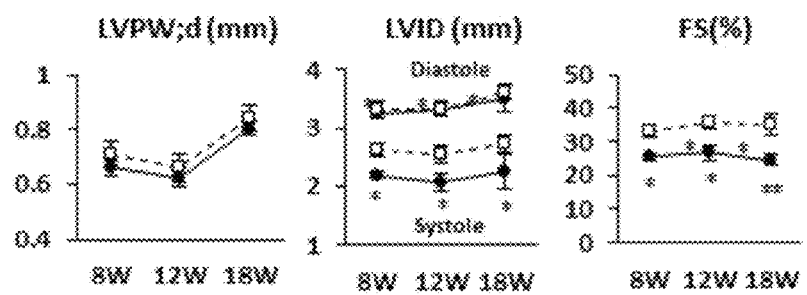
FIG. 3b shows the results of the diastolic left ventricular posterior wall thickness (LVPW; d), the left ventricular end diastolic internal diameter (LVID; d) and percent fractional shortening (% FS) in 8 weeks old, 12 weeks old and 18 weeks old αMHC-Angptl2 Tg mice and wild-type littermates (each group, n=5-7).
Figure 3C:
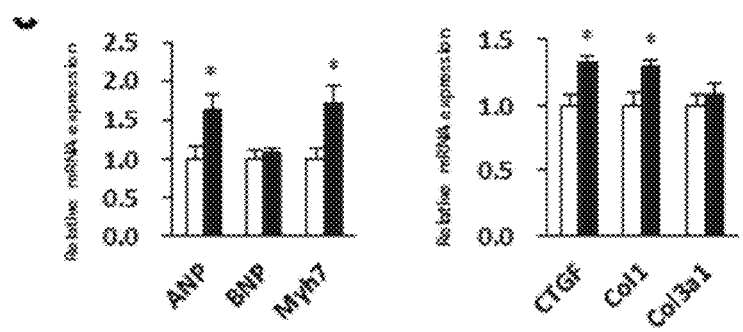
FIG. 3c shows the results of relative expression of genes associated with HF and fibrosis in hearts of 12 weeks old αMHC-Angptl2 Tg mice and wild-type littermates (each group, n=5-7). Values from wild-type (WT) were set to 1. Data are expressed as the mean±SEM. *: $p<0.05$.

As shown in FIG. 3, compared to wild-type littermates, 8-week-old αMHC-Angptl2 Tg mice showed cardiac systolic dysfunction, and 12-week-old transgenics exhibited cardiomyocyte hypertrophy with decreased fractional shortening and increased expression of the heart failure markers ANP and Myh7 and fibrosis markers CTGF and Col1.

Cardiac dysfunction is associated with abnormal $Ca^{2+}$ handling in cardiomyocytes. To assess excitation-contraction (EC) coupling of cardiomyocytes overexpressing ANGPTL2, contractility and $Ca^{2+}$ transients induced by electrical stimulation at 1 Hz was analyzed in single cells isolated from αMHC-Angptl2 Tg and wild-type control mice. The results are shown in FIG. 4. Fractional shortening was markedly reduced in cardiomyocytes overexpressing ANGPTL2 relative to controls (FIG. 4a). In addition, in ANGPTL2-overexpressing cardiomyocytes, the magnitude of electrically evoked $Ca^{2+}$ transients was 68% that of wild-type values (FIGS. 4b and c). The time to peak $[Ca^{2+}]i$ and the time constant of $Ca^{2+}$ transient decay were prolonged in ANGPTL2-overexpressing cardiomyocytes (FIGS. 4b, d and e). Moreover, sarcoplasmic reticulum (SR) $Ca^{2+}$ content in cardiomyocytes from MHC-Angptl2 Tg mice was significantly lower relative to that in wild-type littermates. Overall, these findings indicate that increased ANGPTL2 expression impairs contractility and $Ca^{2+}$ cycling in cardiomyocytes.

Figure 6:
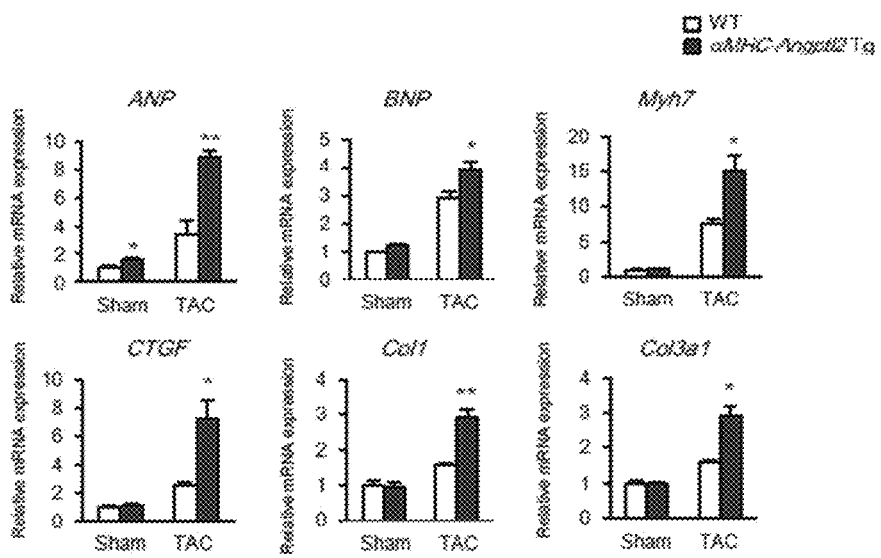
FIG. 6 shows the results of confirming the relative expression of genes associated with heart failure and cardiac fibrosis in the cardiac tissue 3 weeks after the TAC treatment of αMHC-ANGPTL2 Tg mice and wild-type mice. n=6 in each group. Values from WT were set to 1.

Three weeks after TAC, wild-type mice developed adaptive cardiac hypertrophy without left ventricular dilatation, while αMHC-Angptl2 Tg mice developed marked left ventricular dilatation with an advanced decrease in fractional shortening, resulting in HFrEF development accompanied by lung congestion (Data not shown). Cardiac fibrosis, as estimated by histological analysis and marker analysis, was significantly increased in αMHC-Angptl2 Tg mice relative to controls. The results of histological analysis and marker analysis are shown in FIGS. 5 and 6, respectively.

Figure 7:
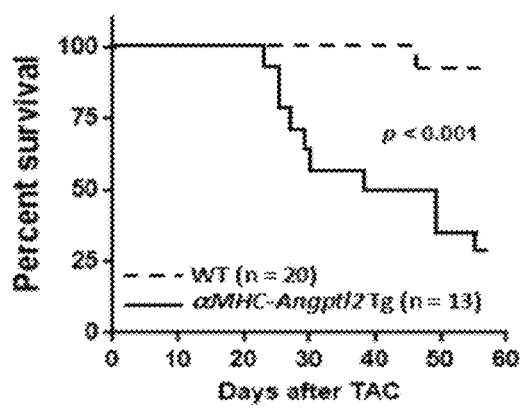
FIG. 7 shows the survival rate after the TAC treatment of αMHC-ANGPTL2 Tg mice (n=13) and wild-type mice (n=28).

By 8 weeks after TAC, most αMHC-Angptl2 Tg mice had died, while few control mice died by that time point. The results are shown in FIG. 7. Moreover, ultrasonic echocardiography revealed that wild-type mice preserved cardiac systolic function, as estimated by fractional shortening, while αMHC-Angptl2 Tg mice analyzed in the Ang II model showed severe cardiac systolic dysfunction due to decreased fractional shortening. Cardiac fibrosis and expression of heart failure and fibrosis markers were significantly increased in αMHC-Angptl2 Tg compared to control mice. These findings indicate that cardiac ANGPTL2 misexpression predisposes mice to HF by reducing cardiac contractility.

(Example 3) Investigation Whether Circulating ANGPTL2 Promotes Pathological Hypertrophy or Cardiac Dysfunction TAC increases circulating ANGPTL2 protein levels. Thus, it is examined whether circulating ANGPTL2 has an endocrine effect on cardiac dysfunction. The present inventors previously reported that diet-induced obese mice show increased ANGPTL2 expression in adipose tissue and increased levels of circulating ANGPTL2 protein (Tabata M. et al. Cell Metab. 10, 178-188 (2009)). Here, two models of genetically obese diabetic mice (db/db and KK-Ay) were used. It observed elevated ANGPTL2 protein levels in circulation relative to controls, whereas ANGPTL2 protein levels in heart tissue were comparable to controls. Ultrasonic echocardiography revealed no cardiac hypertrophy, ventricular dilatation, or cardiac dysfunction in db/db or KK-Ay mice relative to non-obese controls. In both models, ANP, BNP, and Myh7 expression in heart was unchanged relative to controls.

Moreover, transgenic mice overexpressing ANGPTL2 in skin under control of the K14 promoter (K14-Angptl2 Tg mice) showing circulating ANGPTL2 protein levels greater than those in wild-type controls was used. Cardiac ANGPTL2 protein levels were comparable in both of Tg mice and wild-type mice. Ultrasonic echocardiography and RT-PCR analysis revealed no differences in cardiac phenotypes or molecular markers between K14-Angptl2 Tg and wild-type controls, suggesting that circulating ANGPTL2 has no endocrine effect on cardiac remodeling.

Transgenic mice overexpressing ANGPTL2 under control of the aP2 promoter (aP2-Angptl2 Tg mice) also showed increased circulating ANGPTL2 protein levels relative to controls. Although aP2/fatty acid binding protein 4 (FABP4) is reportedly expressed in adipocytes and macrophages, immunoblotting revealed significantly increased ANGPTL2 expression in heart of aP2-Angptl2 Tg mice relative to controls. Interestingly, 8-week-old aP2-Angptl2 Tg mice showed decreased fractional shortening relative to controls and 16-week-old aP2-Angptl2 Tg mice showed cardiomyocyte hypertrophy with decreased fractional shortening. Three weeks after TAC, wild-type mice developed adaptive cardiac hypertrophy without left ventricular dilatation, while aP2-Angptl2 Tg mice developed left ventricular dilatation with an advanced decrease in fractional shortening, resulting in HFrEF with lung congestion. The area of perivascular fibrosis seen in aP2-Angptl2 Tg mice also significantly exceeded that seen in controls. Expression of heart failure and fibrosis markers were also observed. Overall these findings suggest that ANGPTL2 locally-derived from heart, rather than circulating ANGPTL2 originating in other tissue, promotes pathological hypertrophy or cardiac dysfunction.

Figure 8:
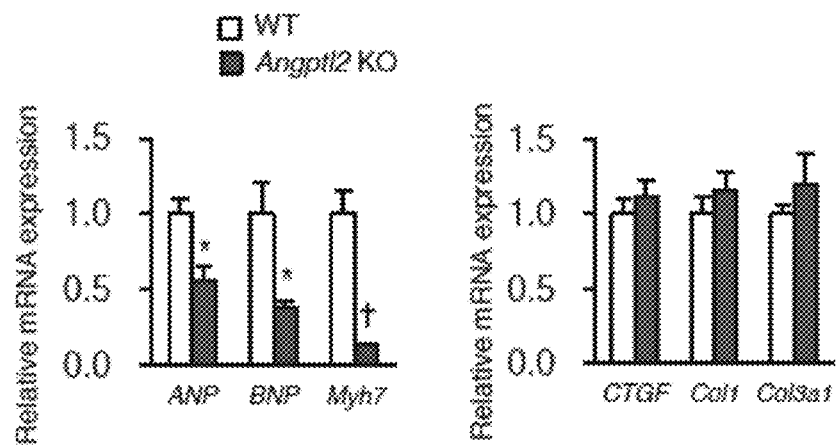
FIG. 8 shows the results of confirming the relative expression of genes associated with heart failure and fibrosis of 12 weeks old Angptl2 KO mice and wild-type litter mice (WT). Values from WT were set to 1.

(Example 4) Investigation Whether Angptl2 KO Mice Progresses from Cardiac Hypertrophy to HF Under Chronic Pressure Overload To assess whether ANGPTL2 deficiency in heart alters pathological remodeling, Angptl2 KO mouse phenotypes were investigated. Angptl2 KO mice are normal at birth and show no gross cardiac phenotypes. Compared to controls, 6-week-old Angptl2 KO mice showed increased cardiac systolic function and 12-week-old Angptl2 KO mice exhibited cardiomyocyte hypertrophy with increased cardiac systolic function (Data not shown). However, expression of heart failure markers in heart of Angptl2 KO mice was relatively decreased (FIG. 8), while fibrosis markers remained unchanged (FIG. 8), suggesting that cardiac hypertrophy seen in Angptl2 KO mice without TAC may not be pathological.

By six weeks after TAC, wild-type controls developed left ventricular dilatation with reduced fractional shortening, leading to HFrEF development. Angptl2 KO mice also showed decreased fractional shortening, but to a lesser degree than littermate controls and they retained adaptive cardiac hypertrophy without ventricular dilatation (Data not shown). ANP, BNP, and Myh7 expression was significantly decreased in Angptl2 KO compared to control mice, whereas fibrosis markers were comparable (Data not shown). These findings suggest that ANGPTL2 deficiency in heart increases cardiac contractility and renders cells resistant to HF development under pressure overload. In the Ang II model, it observed significantly decreased areas of perivascular fibrosis and decreased expression of some heart failure (ANP and Myh7, but not BNP) and fibrosis (CTGF and Col1, but not Col3a1) markers in Angptl2 KO compared to control littermates, suggesting that cardiac ANGPTL2 deficiency antagonizes pathological remodeling.

(Example 5) R-Fatty Acid Oxidation, Mitochondrial Biogenesis, and Intracellular ATP Production Increase in the ANGPTL2-Deficient Heart Cardiac function requires constant intracellular ATP production. Because αMHC-Angptl2 Tg mice develop TAC-induced HF, expression of genes regulating myocardial energy metabolism in αMHC-Angptl2 Tg were compared to those in wild-type controls. Expression of PGC-1α and PPARα (transcription factors regulating R-oxidation and mitochondrial biogenesis), among other genes related to these activities and ATP production, was significantly decreased in 13-week-old αMHC-Angptl2 Tg mice relative to wild-type controls (Data not shown). Conversely, expression of energy-related genes in 13-week-old Angptl2 KO mice was significantly greater than in wild-type controls (Data not shown). Moreover, PGC-1α and PPARα expression and that of CD36 (a receptor for fatty acids) were significantly increased in 6-week-old Angptl2 KO relative to wild-type control mice (Data not shown). Moreover, PPARα and PGC-1α expression and intracellular ATP production were significantly increased in Angptl2 knockdown (KD) primary NRCMs, while PPARα expression (but not PGC-1α) and ATP production were significantly decreased in NRCMs transduced with adenovirus expressing ANGPTL2 (Data not shown). These findings indicate that ANGPTL2 suppression in cardiomyocytes increases expression of genes promoting normal cardiac energy metabolism.

(Example 6) ANGPTL2 Inactivates AKT-SERCA2a Signaling in Heart

Figure 9:
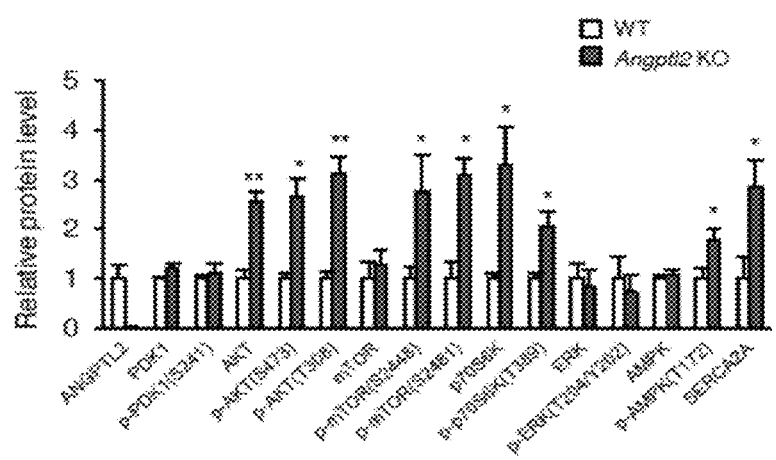
FIG. 9 shows quantitatively the results of immunoblotting of various signaling factors and SERCA2a in the hearts of Angptl2 KO mice and littermate mice (WT). n=3-6 in each group. Values from control were set to 1. Data are expressed as the mean±SEM. *: $p<0.05$, **: $p<0.01$.
Figure 10:
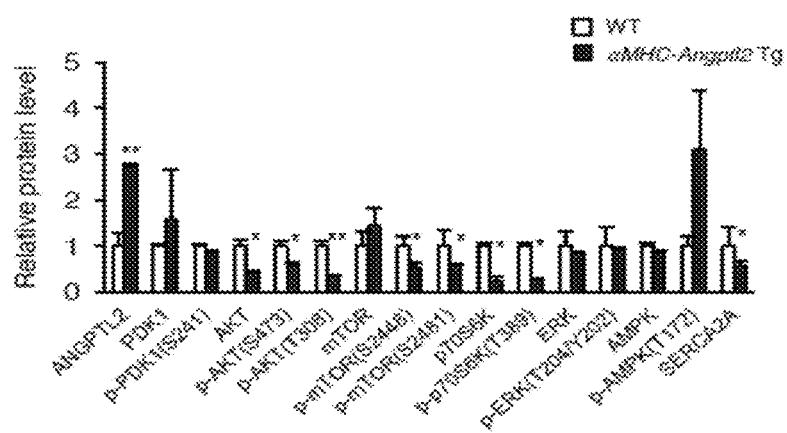
FIG. 10 shows quantitatively the results of immunoblotting of various signaling factors and SERCA2a in the hearts of αMHC-ANGPTL2 Tg mice and littermate mice (WT). n=3-6 in each group. Values from control were set to 1. Data are expressed as the mean±SEM. *: $p<0.05$, **: $p<0.01$.
Figure 11:
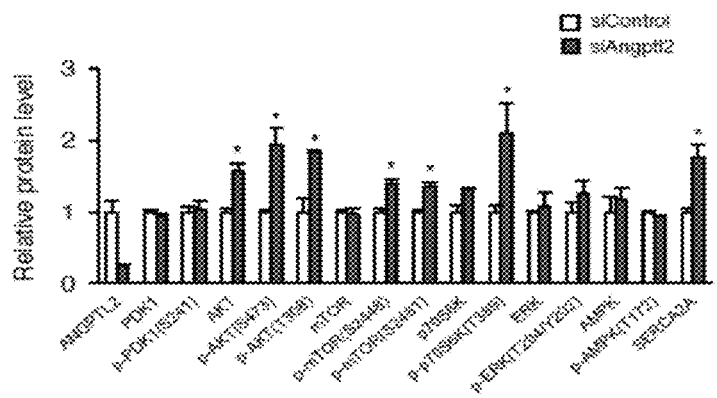
FIG. 11 shows quantitatively the results of immunoblotting of indicated factors in NRCMs transfected with Angptl2 or the control siRNA. n=2-4 in each group. Values from control were set to 1. Data are expressed as the mean±SEM. *: $p<0.05$, **: $p<0.01$.
Figure 12:
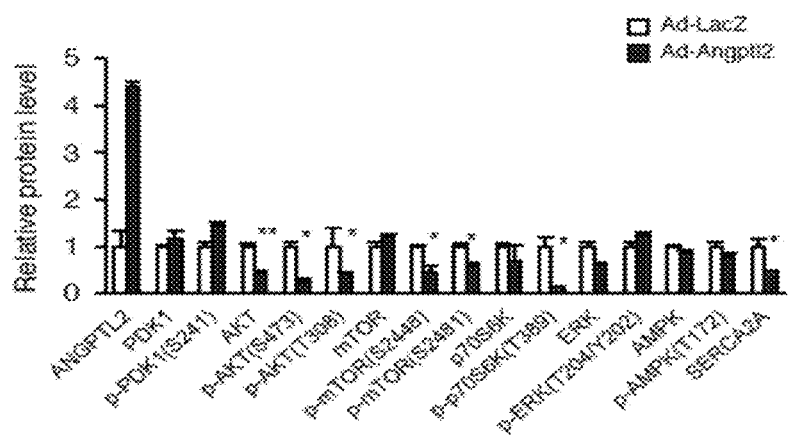
FIG. 12 shows quantitatively the results of immunoblotting of indicated factors in NRCMs transfected with Ad-Angptl2 or the control Ad-LacZ. n=2-4 in each group. Values from control were set to 1. Data are expressed as the mean±SEM. *: $p<0.05$, **: $p<0.01$.

To identify mechanisms linking ANGPTL2 activity with cardiac contractility, by employing a pathway scan assay in which AKT and its effectors mTOR and p70S6K were activated in the heart of Angptl2 KO and wild-type control mice, and those activity were compared each other. The results of Western blotting are shown in FIGS. 9 to 12. It revealed activated AKT signaling in the heart of Angptl2 KO relative to littermate control mice (FIG. 9). SERCA2a protein levels showed a similar increase (FIG. 9). Conversely, AKT signaling was attenuated in the heart of αMHC-Angptl2 Tg mice (FIG. 10), and relative SERCA2a levels were likewise significantly decreased (FIG. 10). It revealed AKT activation and higher SERCA2a protein levels (FIG. 11) in Angptl2 KD NRCMs. Such increased SERCA2a levels were significantly attenuated by overexpression of dominant-negative AKT (dnAKT) (Data not shown). Conversely, AKT signaling was markedly inhibited in NRCMs overexpressing ANGPTL2 (FIG. 12), and SERCA2a protein levels were comparably decreased (FIG. 12). Thus, activation of AKT-SERCA2a signaling following ANGPTL2 loss likely increases cardiac contractility, while ANGPTL2 overexpression promotes the opposite phenotype.

(Example 7) Effect of Activation of Calcineurin-NFAT on Angptl2 mRNA Levels in Cardiomyocytes To determine how ANGPTL2 expression is increased in heart tissue undergoing pathological remodeling, cultured NRCMs was stimulated with factors promoting cardiac hypertrophy. Treatment with Ang II or isoproterenol (Iso) significantly increased Angptl2 mRNA levels in NRCMs. Both Ang II and Iso reportedly promote nuclear translocation of NFAT, a transcription factor underlying development of pathological cardiac hypertrophy. These observations suggest that NFAT activation may increase Angptl2 transcription in cardiomyocytes. Immunocytochemical analysis confirmed that NFATC1 and NFATC4, both expressed in cardiomyocytes, undergo nuclear translocation after Ang II treatment, an activity inhibited by cyclosporine A (CsA). Moreover, Ang II- or Iso-dependent ANGPTL2 up-regulation in NRCMs was blocked by CsA treatment. Ang II treatment also increased ANGPTL2 protein levels in NRCMs, which effect was blocked by CsA. Moreover, overexpression of constitutively active NFAT (CA-NFAT) increased Angptl2 mRNA levels in NRCMs, suggesting that calcineurin-NFAT signaling increases ANGPTL2 expression in cardiomyocytes.

(Example 8) Effect of Endurance Exercise Training on ANGPTL2 Expression

Figure 13:
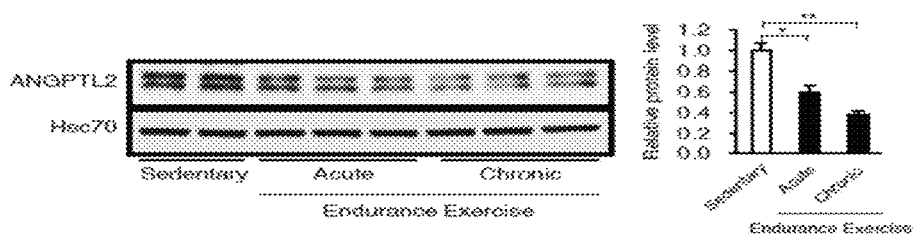
FIG. 13 shows the results of immunoblotting of ANGPTL2 protein from the hearts of control mice without exercise load and mice having undergone acute treadmill running or chronic endurance training. Hsc70 was used as the migration control. Values from control mouse without exercise load were set to 1. n=6-8 in each group.

Cardiac hypertrophy observed in Angptl2 KO mice resembles hypertrophy induced by exercise. Accordingly, Angptl2 KO mice exhibit cardioprotection against pathological cardiac remodeling similarly to exercise-trained mice, suggesting that ANGPTL2 deficiency recapitulates exercise effects. Interestingly, compared to outcomes in sedentary control mice, ANGPTL2 protein levels were markedly decreased in the heart of mice undergoing acute training by treadmill running, and those decreased levels persisted in hearts of mice undergoing chronic training (FIG. 13).

To assess mechanisms underlying this decrease the microRNA.org database, as inhibitory microRNAs reportedly function in cardiovascular disease, was evaluated. Five candidates including miR-135a, miR-204, miR-211, miR-221, and miR-222 were identified. All of them bind to the Angptl2 mRNA 3'UTR, as predicted by the database. Among them, miR-222 expression in heart was recently reported to increase after exercise training in mice (Liu, X., et al. Cell Metab 21, 584-595 (2015)). In vitro, miR-222 or miR-221 overexpression in NRCMs significantly attenuated Angptl2-3'UTR luciferase reporter activity (FIG. 14), effects blocked following deletion of miR-221/222 binding sequences (FIG. 15a). MiR-221/222 KO and miR-221/$222^{Flox/y}$ control mice are subjected to chronic exercise training, and ANGPTL2 protein levels were measured. In miR-221/$222^{Flox/y}$ control mice, ANGPTL2 protein levels in heart tissues of exercised mice were significantly lower than that seen in sedentary mice. In contrast, in miR-221/222 KO mice, an exercise-induced decrease in cardiac ANGPTL2 protein levels did not occur (FIG. 15b). These findings suggest that ANGPTL2 could be a direct miR-221/222 target and that endurance exercise could increase the suppressive effect of these miRs on Angptl2 mRNA levels.

Figure 16:
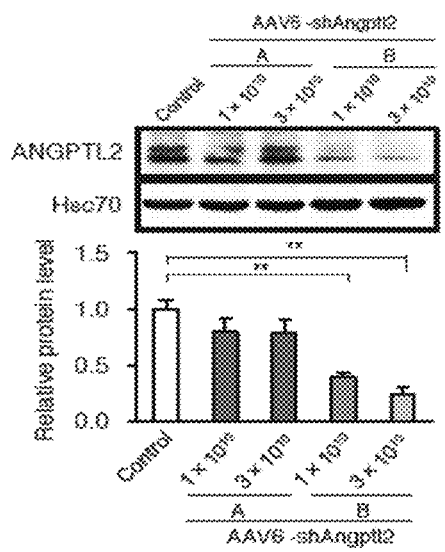
FIG. 16 shows the results of immunoblotting of ANGPTL2 two weeks after intravenous administration of mouse Angptl2 shRNA (AAV6-shAngptl2-A and -B) at $1\times10^{10}$ vg/mouse and $3\times10^{10}$ vg/mouse to wild-type mice. Values from un-injected mouse were set to 1. n=4 in each group.
Figure 17A:
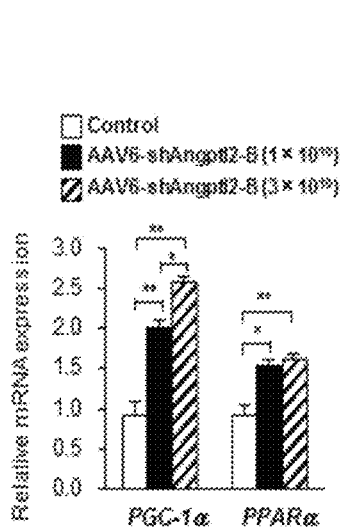
FIG. 17a to FIG. 17b: Like in FIG. 16.
Figure 17B:
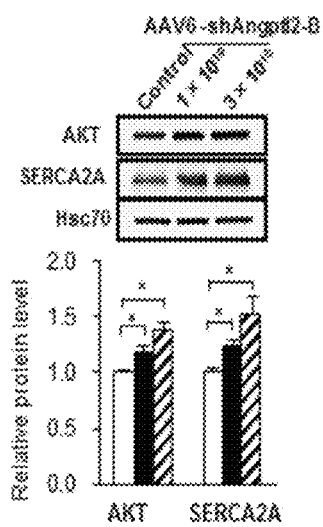

(Example 9) Effect on Blocking ANGPTL2 Up-Regulation in Pathological Hypertrophy in HF Development of Chronic Pressure Overload Mice Whether in vivo administration of anti-ANGPTL2 reagents counteract pathological cardiac remodeling was assessed. Systemic delivery of recombinant adeno-associated viral serotype 6 (AAV6) vector reportedly preferentially transduces cardiac muscle was employed. Angptl2 shRNA cassettes were delivered into mouse heart by intravenous injection of recombinant AAV6 vector expressing Angptl2 shRNA. To do so, two constructs expressing mouse Angptl2 shRNAs (AAV6-shAngptl2-A and -B) were generated, and 1.times.10.sup.10 vg/mouse and 3.times.10.sup.10 vg/mouse of recombinant AAV6-shAngptl2-A or AAV6-shAngptl2-B were intravenously injected into wild-type mice. Two weeks later, ANGPTL2 expression in the heart of mice injected with AAV6-shAngptl2-B was significantly decreased, whereas AAV6-shAngptl2-A construct showed a lower effect compared to AAV6-shAngptl2 at the dose (FIG. 16). Heart tissue of mice injected with AAV6-shAngptl2-B showed increased expression of PGC-1.alpha. and PPAR.alpha. relative to controls and activation of AKT-SERCA2a signaling (FIG. 17).

(Example 10) Confirmation of Effect of Blocking of ANGPTL2 Upregulation Using TAC Model (Experiment 1)

Figure 20:
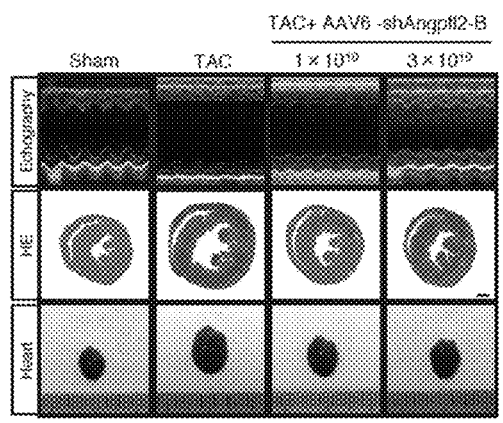
FIG. 20 shows the recording of M-mode echocardiography, the result of HE staining of sections of heart midportion (scale bar: 1 mm) gross appearance of whole heart in control mice, TAC-treated mice, and TAC-treated mice 4 weeks after administration of AAV6-shAngptl2-B.
Figure 21A:
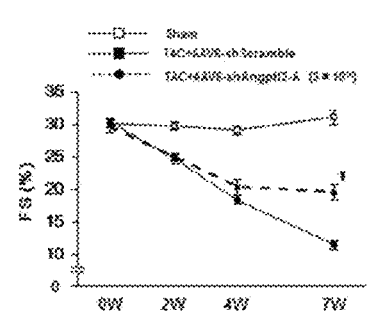
FIG. 21a to FIG. 21d shows the results of comparison of the indicated parameters among TAC-treated mice without virus administration (control) and TAC-model mice obtained by intravenous administration of AAV-shScramble or AAV6-shAngptl2-A at $3\times10^{10}$ vg/mouse. n=10 in each group. Data are expressed as the mean±SEM. **: p<0.01, *: p<0.001.
Figure 21B:
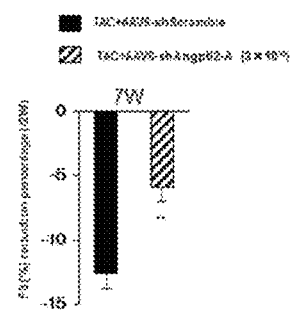
Figure 21C:
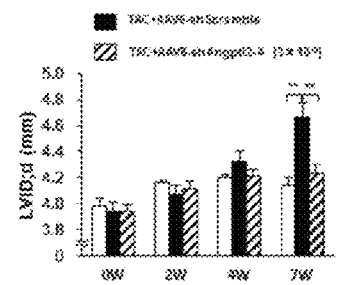
Figure 21D:
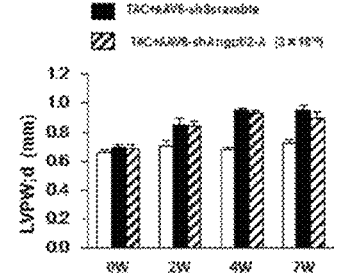

It was assessed whether intravenous injection of AAV6-shAngptl2-B suppresses ANGPTL2 up-regulation in vivo in the TAC model, in which hypertrophy is evident by two weeks after surgery. Mice with TAC-induced cardiac dysfunction two weeks after surgery were divided into three groups, and then mice were intravenously injected with no virus (controls), $1 \times 10^{10}$ vg/mouse of recombinant AAV6-shAngptl2-B, and $3 \times 10^{10}$ vg/mouse of the same construct. Two weeks after injection, cardiac function was examined by ultrasonic echocardiography every two weeks. Both AAV6-shAngptl2-B doses suppressed ANGPTL2 up-regulation in pathological cardiac remodeling under pressure overload (FIG. 18). Control mice showed left ventricular dilatation with reduced fractional shortening, whereas cardiac dysfunction was attenuated and dilatation of the left ventricle was blocked in mice injected with either AAV6-shAngptl2-B dose (FIGS. 19 and 20). Heart weight/body weight ratios were decreased in mice injected with either dose of AAV6-shAngptl2-B compared to controls. Finally, whereas expression of ANP, BNP, and Myh7 was significantly increased in control heart, up-regulated ANP and Myh7 expression was significantly blocked in mice injected recombinant AAV6-shAngptl2-B (Data not shown).

(Example 11) Confirmation of Effect of Blocking of ANGPTL2 Upregulation Using TAC Model (Experiment 2)

In the same manner as in Example 10, it was investigated in vivo whether intravenous injection of AAV6-shANGPTL2-B or AAV6-shANGPTL2-A suppresses up-regulation of ANGPTL2, using the TAC model. In this example, AAV-shScramble was intravenously administered to the TAC model, as control. In addition, cardiac systolic function is examined by ultrasonic echocardiography 2 weeks and 5 weeks after the administration.

Administration of AAV6-shANGPTL2-B showed an advantageous effect in comparison with the TAC model administered with AAV-shScramble like as in Example 10.

The results of administration of AAV6-shANGPTL2-A are shown in FIG. 21. In addition to AAV6-shANGPTL2-B, administration of AAV6-shANGPTL2-A also showed improvement in cardiac dysfunction compared to the control mice.

(Example 12) Suppression Effect of ANGPTL2 in Human iPS-Derived Cardiomyocytes

Figure 22A:
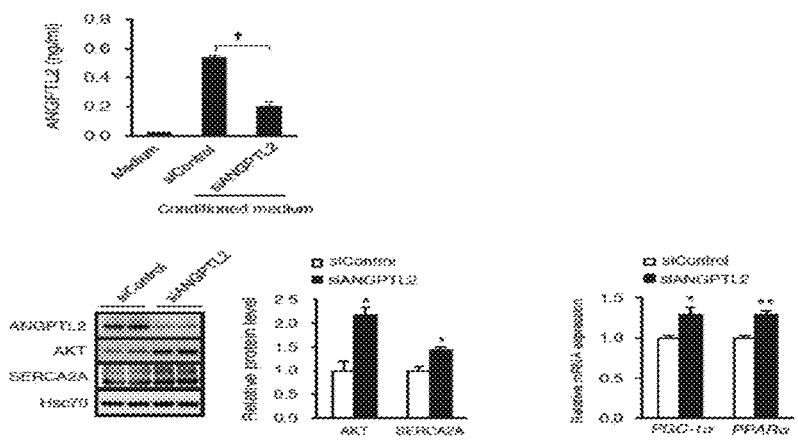
Figure 23:
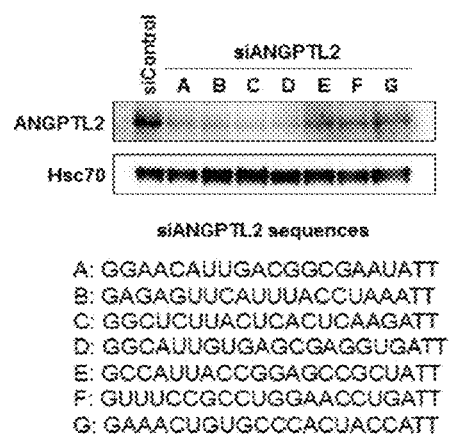
FIG. 23 shows the results of detecting the ANGPTL2 protein level in the medium by Western blot, in human iPS-derived cardiomyocytes transfected with seven kinds of siRNA targeting ANGPTL2 (siANGPTL2-A to G: SEQ ID NO. 29-35) or control siRNA. Hsc70 was served as a loading control.

In human cardiomyocytes differentiated from iPS cells derived from human fibroblasts, it was examined whether ANGPTL2 suppression would activate AKT-SERCA2a signaling and enhance energy metabolism. The results are shown in FIGS. 22 and 23. ANGPTL2 production and secretion were suppressed while AKT-SERCA2a signaling and PGC-1α and PPARα expression were activated in cardiomyocytes transfected with the siRNA targeting human ANGPTL2 (ANGPTL2 siRNA). Moreover, no changes was observed in beating rate, cellular characteristics (including size and shape), or frequency of cell death in cardiomyocytes transfected with ANGPTL2 siRNA relative to control human iPS-derived cardiomyocytes, suggesting a lack of cardio-toxicity. As shown in FIG. 23, examined seven kinds of siRNA targeting human ANGPTL2 significantly reduced the expression of ANGPTL2 protein.

(Example 13) Cardiac ANGPTL2 Production in HF Patients

To investigate whether ANGPTL2 functions in pathological cardiac remodeling, ANGPTL2 protein levels in heart tissue obtained at autopsy from either patients diagnosed with chronic heart failure or individuals who died in circumstances not related to heart disease were measured. Immunohistochemical analysis showed that in HF patients, ANGPTL2 protein was abundantly expressed primarily in cardiomyocytes and capillary vessel endothelial cells but not in cardiac fibroblasts. By contrast, in control individuals, ANGPTL2 protein was expressed at lower levels in heart.

The coronary sinus (CS) drains blood from the heart. Thus, potential differences in ANGPTL2 concentrations between the CS and the aortic root (Ao) would reflect ANGPTL2 secretion from heart tissue. It investigated whether such secretion occurs in patients with cardiac dysfunction. ANGPTL2 concentrations in the CS and Ao in 58 patients with non-secondary and non-familial DCM were compared, resulting in that significantly elevated (>35% increase) ANGPTL2 production in heart tissue of 23 patients were observed. Between the 23 patients and the 35 patients that did not show this pattern, there was no difference in severity of cardiac dysfunction, as estimated by several clinical indices. Patients that showed signs of increased cardiac ANGPTL2 secretion were generally older and exhibited mildly enlarged LVDd diameter relative to other patients. The results are shown in Table 1 below.

TABLE 1

| DCM Patient Clinical Characteristics. | | | |
|---|---|---|---|
| Number | Activated Group (ANGPTL2 levels: (Cs-Ao)*100/Ao > 35%) 23 | Non-Activated Group (ANGPTL2 levels: (Cs-Ao)*100/Ao ≤ 35%) 35 | p |
| Age | 59.17 ± 2.50 | 51.89 ± 2.10 | <0.05 |
| Sex (male/female) | 15/8 | 25/10 | |
| NYHA (I/II/III) | 12/9/2 | 14/18/3 | |
| BNP (pg/ml) | 217.04 ± 43.63 | 178.65 ± 50.58 | n.s. |
| Cardiac Catheterization Analysis | | | |
| ANGPTL2 levels in Ao (ng/ml) | 2.41 ± 0.17 | 2.50 ± 0.16 | n.s. |
| ANGPTL2 levels in Cs (ng/ml) | 4.56 ± 0.30 | 2.09 ± 0.18 | <0.01 |
| Step-up of ANGPTL2 levels from Ao to Cs ((Cs-Ao)*100/Ao (%)) | 97.62 ± 11.06 | −18.18 ± 4.05 | <0.01 |
| EF (%) | 32.08 ± 2.14 | 31.54 ± 1.91 | n.s. |
| CI (L/min/m$^2$) | 2.56 ± 0.12 | 2.75 ± 0.11 | n.s. |
| PCWP (mmHg) | 11.59 ± 0.96 | 12.70 ± 1.08 | n.s. |
| Ultrasonic Echocardiographic Analysis | | | |
| LVDd (mm) | 59.09 ± 1.16 | 64.57 ± 1.51 | <0.01 |
| LAD (mm) | 40.61 ± 1.72 | 41.07 ± 1.58 | n.s. |

TABLE 1-continued

DCM Patient Clinical Characteristics.

| Number | Activated Group (ANGPTL2 levels: (Cs-Ao)*100/Ao > 35%) 23 | Non-Activated Group (ANGPTL2 levels: (Cs-Ao)*100/Ao ≤ 35%) 35 | p |
|---|---|---|---|
| LVMI (g/m$^2$) | 153.46 ± 8.22 | 179.38 ± 12.73 | n.s. |
| % FS (%) | 18.54 ± 1.43 | 16.03 ± 1.00 | n.s. |

Values are mean ± SEM or number (n) and percentage (%) for categorical variabies.
DCM = dilated cardiomyopathy; Ao = aortic root; Cs = coronary sinus; EF = ejection fraction; CI = cardiac index; PCWP = pulmonary capillary wedge pressure; LVDd = left ventricuiar end-diastolic dimension; LAD = left atrial dimension; LVM = left ventricular mass index; FS = fractional shortening; n.s. = not significant.

The above detailed description merely illustrates objects and subjects of the present invention, and does not limit the accompanying Claims. Without departing from the accompanying Claims, various modifications and alterations to the described embodiments will be apparent to those skilled in the art in view of the teachings herein.

INDUSTRIAL APPLICABILITY

The present invention is useful for suppressing expression of the angiopoietin-like protein 2 gene in cardiomyocytes, and the present invention is useful as a pharmaceutical composition for treatment or prevention of heart failure.

[Sequence List]

The invention claimed is:

1. A method for treating or preventing heart failure, comprising administering a pharmaceutical composition comprising an expression vector containing a DNA sequence encoding RNA comprising a sense strand sequence of consecutive 18 to 29 nucleotides from angiopoietin-like protein 2 mRNA or the alternative splicing type RNA thereof, and an antisense strand sequence complementary to the sense strand sequence under control of a promoter and a pharmaceutically acceptable carrier to a mammal subject in need of treatment or prevention of heart failure in an amount effective for treating or preventing heart failure of the subject,
  wherein the expression vector has delivery selectivity into cardiomyocytes and the sense strand sequence and antisense strand sequence are adapted for use in preparing siRNA, wherein the siRNA, when transduced into a cardiomyocyte cell, suppresses expression of the angiopoietin-like protein 2 gene in the cardiomyocyte cell.

2. The method according to claim 1,
  wherein the DNA sequence comprises a sequence encoding RNA comprising the sense strand sequence, the antisense strand sequence and a hairpin type RNA sequence composed of a single strand hairpin sequence bonding the sense strand sequence and the antisense strand sequence via a covalent bond, and
  wherein the DNA sequence is adapted for use such that, when the hairpin sequence is processed by Dicer, an intracellular RNase, siRNA comprising the sense strand sequence and the antisense strand sequence is formed.

3. The method according to claim 1, wherein the mammal subject in need of treatment or prevention of heart failure is a patient in which the expression level of angiopoietin-like protein 2 in the blood of the coronary sinus thereof is higher than the expression level in the blood of the aortic root thereof.

4. The method according to claim 1, wherein the sense strand sequence is any one of SEQ ID NO. 2 to SEQ ID NO. 8, and wherein:

```
SEQ ID NO. 2:
GGAACAUUGACGGCGAAUA

SEQ ID NO. 3:
GAGAGUUCAUUUACCUAAA

SEQ ID NO. 4:
GGCUCUUACUCACUCAAGA

SEQ ID NO. 5:
GGCAUUGUGAGCGAGGUGA

SEQ ID NO. 6:
GCCAUUACCGGAGCCGCUA

SEQ ID NO. 7:
GUUUCCGCCUGGAACCUGA

SEQ ID NO. 8:
GAAACUGUGCCCACUACCA.
```

5. The method according to claim 1, wherein the DNA sequence comprises a nucleotide sequence of any one of SEQ ID NO. 9 to SEQ ID NO. 15, and wherein:

```
SEQ ID NO. 9:
GGAACATTGACGGCGAATA

SEQ ID NO. 10:
GAGAGTTCATTTACCTAAA

SEQ ID NO. 11:
GGCTCTTACTCACTCAAGA

SEQ ID NO. 12:
GGCATTGTGAGCGAGGTGA
```

```
-continued
SEQ ID NO. 13:
GCCATTACCGGAGCCGCTA

SEQ ID NO. 14:
GTTTCCGCCTGGAACCTGA

SEQ ID NO. 15:
GAAACTGTGCCCACTACCA.
```

6. The method according to claim 1, wherein the mammal subject is a dilated cardiomyopathy patient.

7. The method according to claim 1, wherein the expression vector is a plasmid or a viral vector.

8. The method according to claim 7, wherein the viral vector is an adenoviral vector, an adeno-associated viral vector, a lentiviral vector or a retroviral vector.

9. The method according to claim 8, wherein the viral vector is an adeno-associated virus serotype 6 vector.

10. A method for treating or preventing heart failure, comprising administrating a pharmaceutical composition for treating or preventing heart failure comprising siRNA comprising a sense strand sequence of consecutive 18 to 29 nucleotides from angiopoietin-like protein 2 mRNA or alternative splicing type RNA thereof and an antisense strand sequence complementary to the sense strand sequence and a pharmaceutically acceptable carrier to a mammal subject in need of treatment or prevention of heart failure in an amount effective for treating or preventing heart failure of the subject,
  wherein the siRNA targets angiopoietin-like protein 2 gene in cardiomyocytes and is adapted for use such that the siRNA, when transduced into a cardiomyocyte cell, suppresses expression of the angiopoietin-like protein 2 gene in the cardiomyocyte cell.

11. The method according to claim 10, wherein the sense strand sequence comprises a nucleotide sequence of any one of SEQ ID NO. 2 to SEQ ID NO. 8, and wherein:

```
SEQ ID NO. 2:
GGAACAUUGACGGCGAAUA

SEQ ID NO. 3:
GAGAGUUCAUUUACCUAAA

SEQ ID NO. 4:
GGCUCUUACUCACUCAAGA

SEQ ID NO. 5:
GGCAUUGUGAGCGAGGUGA

SEQ ID NO. 6:
GCCAUUACCGGAGCCGCUA

SEQ ID NO. 7:
GUUUCCGCCUGGAACCUGA

SEQ ID NO. 8:
GAAACUGUGCCCACUACCA.
```

12. The method according to claim 10, wherein the mammal subject in need of treatment or prevention of heart failure is a patient in which the expression level of angiopoietin-like protein 2 in the blood of the coronary sinus thereof is higher than the expression level in the blood of the aortic root thereof.

13. The method according to claim 10, wherein the mammal subject is a dilated cardiomyopathy patient.

* * * * *

SEQUENCE LISTING

```
<160> NUMBER OF SEQ ID NOS: 38

<210> SEQ ID NO 1
<211> LENGTH: 3707
<212> TYPE: DNA
<213> ORGANISM: Homo sapiens

<400> SEQUENCE: 1
ggggcctgcc gaggccgcca aagcgggctg ggcgggaggg gccaggccag ctggggccgg      60
agctcgtgtg acatcaccgg gcggcccgcc tctgtctggg gctgagggga ggcccggagc     120 cttttctgggg cctgggggat cctcttgcac tggtgggtgg agagaagcgc ctgcagccaa    180
ccagggtcag gctgtgctca cagtttcctc tggcggcatg taaaggctcc acaaaggagt    240
tgggagttca aatgaggctg ctgcggacgg cctgaggatg daccccaagc cctggacctg    300
ccgagcgtgg cactgaggca gcggctgacg ctactgtgag ggaaagaagg ttgtgagcag    360
ccccgcagga cccctggcca gccctggccc cagcctctgc cggagccctc tgtggaggca    420
gagccagtgg agcccagtga ggcagggctg cttggcagcc accggcctgc aactcaggaa    480
cccctccaga ggccatggac aggctgcccc gctgacggcc agggtgaagc atgtgaggag    540
ccgccccgga gccaagcagg agggaagagg ctttcataga ttctattcac aaagaataac    600
caccattttg caaggaccat gaggccactg tgcgtgacat gctggtggct cggactgctg    660
gctgccatgg gagctgttgc aggccaggag gacggttttg agggcactga ggagggctcg    720
ccaagagagt tcatttacct aaacaggtac aagcgggcgg gcgagtccca ggacaagtgc    780
acctacacct tcattgtgcc ccagcagcgg gtcacgggtg ccatctgcgt caactccaag    840
gagcctgagg tgcttctgga gaaccgagtg cataagcagg agctagagct gctcaacaat    900
gagctgctca agcagaagcg gcagatcgag acgctgcagc agctggtgga ggtggacggc    960
ggcattgtga gcgaggtgaa gctgctgcgc aaggagagcc gcaacatgaa ctcgcgggtc   1020
acgcagctct acatgcagct cctgcacgag atcatccgca agcgggacaa cgcgttggag   1080
ctctcccagc tggagaacag gatcctgaac cagacagccg acatgctgca gctggccagc   1140
```

```
aagtacaagg acctggagca caagtaccag cacctggcca cactggccca caaccaatca    1200
gagatcatcg cgcagcttga ggagcactgc cagagggtgc cctcggccag gcccgtcccc    1260
cagccacccc ccgctgcccc gccccgggtc taccaaccac ccacctacaa ccgcatcatc    1320
aaccagatct ctaccaacga gatccagagt gaccagaacc tgaaggtgct gccaccccct    1380
ctgcccacta tgcccactct caccagcctc ccatcttcca ccgacaagcc gtcgggccca    1440
tggagagact gcctgcaggc cctggaggat ggccacgaca ccagctccat ctacctggtg    1500
aagccggaga caccaaccg cctcatgcag gtgtggtgcg accagagaca cgaccccggg    1560
ggctggaccg tcatccagag acgcctggat ggctctgtta acttcttcag gaactgggag    1620
acgtacaagc aagggtttgg gaacattgac ggcgaatact ggctgggcct ggagaacatt    1680
tactggctga cgaaccaagg caactacaaa ctcctggtga ccatggagga ctggtccggc    1740
cgcaaagtct ttgcagaata cgccagtttc cgcctggaac ctgagagcga gtattataag    1800
ctgcggctgg ggcgctacca tggcaatgcg ggtgactcct ttacatggca aacggcaag    1860 cagttcacca ccctggacag agatcatgat gtctacacag gaaactgtgc ccactaccag    1920
aagggaggct ggtggtataa cgcctgtgcc cactccaacc tcaacggggt ctggtaccgc    1980
gggggccatt accggagccg ctaccaggac ggagtctact gggctgagtt ccgaggaggc    2040
tcttactcac tcaagaaagt ggtgatgatg atccgaccga accccaacac cttccactaa    2100
gccagctccc cctcctgacc tctcgtggcc attgccagga gcccaccctg gtcacgctgg    2160
ccacagcaca aagaacaact cctcaccagt tcatcctgag gctgggagga ccggatgct    2220 ggattctgtt ttccgaagtc actgcagcgg atgatggaac tgaatcgata cggtgttttc    2280
tgtccctcct actttccttc acaccagaca gcccctcatg tctccaggac aggacaggac    2340
tacagacaac tctttcttta aataaattaa gtctctacaa taaaaacaca actgcaaagt    2400
accttcataa tatacatgtg tatgagcctc ccttgtgcac gtatgtgtat accacatata    2460
tatgcattta gatatacatc acatgtgata tatctagatc catatatagg tttgccttag    2520
atacctaaat acacatatat tcagttctca gatgttgaag ctgtcaccag cagctttgct    2580
cttaggagaa aagcatttca ttagtgttgt attacttgag tctaagggta gatcacagac    2640
tgtgtggtct caactgaaag gatcaccctt ggcatctgtg tgcctggatt cttccagaat    2700
gtctacaatg ctaatctctc acatagaggt tcccagcttc ttaagaaccc cttttggcac    2760
ctaatcaaat ttcaaaatcc ctcccccac attttcatac ttttccccat tctcaggact    2820
tttcaccatc catcacccac ttatcccttc atttgacacc attcattaag tgccttctgt    2880
gtgtcagtcc ctggccactc actgcagttc aaggccccct ttccgctctg ctgtactcct    2940
cgcctaccta ctccttgcct tttctgtcgc acagcccctt ctttccaggc gagattcctc    3000
agcttctgag taggaaacac tccgggctcc aggtttctgg ttgggaaggg aaggccaggc    3060
caaaagctcc accggccgta tagataatgt actcgcagtt ttgtatcttc cattcatact    3120
ttaacctaca ggtcatttga gtcttcacac aaataataac ctatctggcc aggagaatta    3180
tctcagaaca gaagtcatca gatcatcaga gccccccagat ggctacagac cagagattcc    3240
acgctctcag gctgactaga gtccgcatct catctccaaa ctacacttcc ctggagaaca    3300
agtgccacaa aaatgaaaac aggccacttc tcaggagttg aataatcagg ggtcaccgga    3360
ccccttggtt gatgcactgc agcatggtgg ctttctgagt cctgttggcc accaagtgtc    3420
agcctcagca ctcccgggac tattgccaag aaggggcaag ggatgagtca agaaggtgag    3480
```

-continued

```
acccttcccg gtgggcacgt gggccaggct gtgtgagatg ttggatgttt ggtactgtcc    3540
atgtctgggt gtgtgcctat tacctcagca tttctcacaa agtgtaccat gtagcatgtt    3600
ttgtgtatat aaaagggagg gttttttttaa aaatatattc ccagattatc cttgtaatga    3660
cacgaatctg caataaaagc catcagtgct atttggatgt atctaca                  3707
```

```
<210> SEQ ID NO 2
<211> LENGTH: 19
<212> TYPE: RNA
<213> ORGANISM: Artificial Sequence
<220> FEATURE:
<223> OTHER INFORMATION: partial sequence of human Angptl2

<400> SEQUENCE: 2
ggaacauuga cggcgaaua                                                  19

<210> SEQ ID NO 3
<211> LENGTH: 19
<212> TYPE: RNA
<213> ORGANISM: Artificial Sequence
<220> FEATURE:
<223> OTHER INFORMATION: partial sequence of human Angptl2

<400> SEQUENCE: 3
gagaguucau uuaccuaaa                                                  19

<210> SEQ ID NO 4
<211> LENGTH: 19
<212> TYPE: RNA
<213> ORGANISM: Artificial Sequence
<220> FEATURE:
<223> OTHER INFORMATION: partial sequence of human Angptl2

<400> SEQUENCE: 4
ggcucuuacu cacucaaga                                                  19

<210> SEQ ID NO 5
<211> LENGTH: 19
<212> TYPE: RNA
<213> ORGANISM: Artificial Sequence
<220> FEATURE:
<223> OTHER INFORMATION: partial sequence of human Angptl2

<400> SEQUENCE: 5
ggcauuguga gcgagguga                                                  19

<210> SEQ ID NO 6
<211> LENGTH: 19
<212> TYPE: RNA
<213> ORGANISM: Artificial Sequence
<220> FEATURE:
<223> OTHER INFORMATION: partial sequence of human Angptl2

<400> SEQUENCE: 6
gccauuaccg gagccgcua                                                  19

<210> SEQ ID NO 7
<211> LENGTH: 19
<212> TYPE: RNA
<213> ORGANISM: Artificial Sequence
<220> FEATURE:
<223> OTHER INFORMATION: partial sequence of human Angptl2

<400> SEQUENCE: 7
guuuccgccu ggaaccuga                                                  19
```

<210> SEQ ID NO 8
<211> LENGTH: 19
<212> TYPE: RNA
<213> ORGANISM: Artificial Sequence
<220> FEATURE:
<223> OTHER INFORMATION: partial sequence of human Angptl2

<400> SEQUENCE: 8
gaaacugugc ccacuacca                                               19

<210> SEQ ID NO 9
<211> LENGTH: 19
<212> TYPE: DNA
<213> ORGANISM: Artificial Sequence
<220> FEATURE:
<223> OTHER INFORMATION: partial sequence of human Angptl2

<400> SEQUENCE: 9
ggaacattga cggcgaata                                               19

<210> SEQ ID NO 10
<211> LENGTH: 19
<212> TYPE: DNA
<213> ORGANISM: Artificial Sequence
<220> FEATURE:
<223> OTHER INFORMATION: partial sequence of human Angptl2

<400> SEQUENCE: 10
gagagttcat ttacctaaa                                               19

<210> SEQ ID NO 11
<211> LENGTH: 19
<212> TYPE: DNA
<213> ORGANISM: Artificial Sequence
<220> FEATURE:
<223> OTHER INFORMATION: partial sequence of human Angptl2

<400> SEQUENCE: 11
ggctcttact cactcaaga                                               19

<210> SEQ ID NO 12
<211> LENGTH: 19
<212> TYPE: DNA
<213> ORGANISM: Artificial Sequence
<220> FEATURE:
<223> OTHER INFORMATION: partial sequence of human Angptl2

<400> SEQUENCE: 12
ggcattgtga gcgaggtga                                               19

<210> SEQ ID NO 13
<211> LENGTH: 19
<212> TYPE: DNA
<213> ORGANISM: Artificial Sequence
<220> FEATURE:
<223> OTHER INFORMATION: partial sequence of human Angptl2

<400> SEQUENCE: 13
gccattaccg gagccgcta                                               19

<210> SEQ ID NO 14
<211> LENGTH: 19
<212> TYPE: DNA
<213> ORGANISM: Artificial Sequence
<220> FEATURE:

<223> OTHER INFORMATION: partial sequence of human Angptl2

<400> SEQUENCE: 14
gtttccgcct ggaacctga                                                    19

<210> SEQ ID NO 15
<211> LENGTH: 19
<212> TYPE: DNA
<213> ORGANISM: Artificial Sequence
<220> FEATURE:
<223> OTHER INFORMATION: partial sequence of human Angptl2

<400> SEQUENCE: 15
gaaactgtgc ccactacca                                                    19

<210> SEQ ID NO 16
<211> LENGTH: 15
<212> TYPE: DNA
<213> ORGANISM: Artificial Sequence
<220> FEATURE:
<223> OTHER INFORMATION: binding sequesnce

<400> SEQUENCE: 16
tagtgctcct ggttg                                                        15

<210> SEQ ID NO 17
<211> LENGTH: 15
<212> TYPE: DNA
<213> ORGANISM: Artificial Sequence
<220> FEATURE:
<223> OTHER INFORMATION: binding sequence

<400> SEQUENCE: 17
caaccaggag cacta                                                        15

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
acttctacat gagatcattc                                                   20

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
ggtattctca ggcttcacca ggta                                              24

<210> SEQ ID NO 20
<211> LENGTH: 21
<212> TYPE: DNA
<213> ORGANISM: Artificial Sequence
<220> FEATURE:
<223> OTHER INFORMATION: partial sequence of rat Angptl2

<400> SEQUENCE: 20
ggaucuuacu cacucaagat t                                                 21

```
<210> SEQ ID NO 21
<211> LENGTH: 21
<212> TYPE: DNA
<213> ORGANISM: Artificial Sequence
<220> FEATURE:
<223> OTHER INFORMATION: partial sequence of rat Angptl2

<400> SEQUENCE: 21
gagaguacau uuaccucaat t                                            21

<210> SEQ ID NO 22
<211> LENGTH: 21
<212> TYPE: DNA
<213> ORGANISM: Artificial Sequence
<220> FEATURE:
<223> OTHER INFORMATION: partial sequence of rat Angptl2

<400> SEQUENCE: 22
ccagaaagcg aguacuauat t                                            21

<210> SEQ ID NO 23
<211> LENGTH: 35
<212> TYPE: DNA
<213> ORGANISM: Artificial Sequence
<220> FEATURE:
<223> OTHER INFORMATION: primer

<400> SEQUENCE: 23
catttctcat gttctgtgta tatataaaag ggagg                             35

<210> SEQ ID NO 24
<211> LENGTH: 32
<212> TYPE: DNA
<213> ORGANISM: Artificial Sequence
<220> FEATURE:
<223> OTHER INFORMATION: primer

<400> SEQUENCE: 24
agaacatgag aaatgctgag gtaacagggc ag                                32

<210> SEQ ID NO 25
<211> LENGTH: 65
<212> TYPE: DNA
<213> ORGANISM: Artificial Sequence
<220> FEATURE:
<223> OTHER INFORMATION: mouse Angptl2 shRNA

<400> SEQUENCE: 25
ctagagagag tacatttacc tcaatagtgc tcctggttgt tgaggtaaat gtactctctt  60
tttta                                                              65

<210> SEQ ID NO 26
<211> LENGTH: 65
<212> TYPE: DNA
<213> ORGANISM: Artificial Sequence
<220> FEATURE:
<223> OTHER INFORMATION: mouse Angptl2 shRNA

<400> SEQUENCE: 26
ctagtaaaaa agagagtaca tttacctcaa caaccaggag cactattgag gtaaatgtac  60
tctct                                                              65

<210> SEQ ID NO 27
<211> LENGTH: 67
<212> TYPE: DNA
```

```
<213> ORGANISM: Artificial Sequence
<220> FEATURE:
<223> OTHER INFORMATION: mouse Angptl2 shRNA

<400> SEQUENCE: 27
ctagagccag aaagcgagta ctatatagtg ctcctggttg tatagtactc gctttctggc    60
tttttta                                                              67

<210> SEQ ID NO 28
<211> LENGTH: 67
<212> TYPE: DNA
<213> ORGANISM: Artificial Sequence
<220> FEATURE:
<223> OTHER INFORMATION: mouse Angptl2 shRNA

<400> SEQUENCE: 28
ctagtaaaaa agccagaaag cgagtactat acaaccagga gcactatata gtactcgctt    60
tctggct                                                              67

<210> SEQ ID NO 29
<211> LENGTH: 21
<212> TYPE: DNA
<213> ORGANISM: Artificial Sequence
<220> FEATURE:
<223> OTHER INFORMATION: synthetic nucleotides

<400> SEQUENCE: 29
ggaacauuga cggcgaauat t                                              21

<210> SEQ ID NO 30
<211> LENGTH: 21
<212> TYPE: DNA
<213> ORGANISM: Artificial Sequence
<220> FEATURE:
<223> OTHER INFORMATION: synthetic nucleotides

<400> SEQUENCE: 30
gagaguucau uuaccuaaat t                                              21

<210> SEQ ID NO 31
<211> LENGTH: 21
<212> TYPE: DNA
<213> ORGANISM: Artificial Sequence
<220> FEATURE:
<223> OTHER INFORMATION: synthetic nucleotides

<400> SEQUENCE: 31
ggcucuuacu cacucaagat t                                              21

<210> SEQ ID NO 32
<211> LENGTH: 21
<212> TYPE: DNA
<213> ORGANISM: Artificial Sequence
<220> FEATURE:
<223> OTHER INFORMATION: synthetic nucleotides

<400> SEQUENCE: 32
ggcauuguga gcgaggugat t                                              21

<210> SEQ ID NO 33
<211> LENGTH: 21
<212> TYPE: DNA
<213> ORGANISM: Artificial Sequence
<220> FEATURE:
<223> OTHER INFORMATION: synthetic nucleotides
```

```
<400> SEQUENCE: 33
gccauuaccg gagccgcuat t                                              21

<210> SEQ ID NO 34
<211> LENGTH: 21
<212> TYPE: DNA
<213> ORGANISM: Artificial Sequence
<220> FEATURE:
<223> OTHER INFORMATION: synthetic nucleotides

<400> SEQUENCE: 34
guuuccgccu ggaaccugat t                                              21

<210> SEQ ID NO 35
<211> LENGTH: 21
<212> TYPE: DNA
<213> ORGANISM: Artificial Sequence
<220> FEATURE:
<223> OTHER INFORMATION: synthetic nucleotides

<400> SEQUENCE: 35
gaaacugugc ccacuaccat t                                              21

<210> SEQ ID NO 36
<211> LENGTH: 18
<212> TYPE: PRT
<213> ORGANISM: Artificial Sequence
<220> FEATURE:
<223> OTHER INFORMATION: synthetic peptide

<400> SEQUENCE: 36

Ser Phe Arg Leu Glu Pro Glu Ser Glu Tyr Tyr Lys Leu Arg Leu Gly
1               5                   10                  15

Arg Tyr

<210> SEQ ID NO 37
<211> LENGTH: 67
<212> TYPE: DNA
<213> ORGANISM: Artificial Sequence
<220> FEATURE:
<223> OTHER INFORMATION: synthetic DNA

<400> SEQUENCE: 37
ctagagtctt aatcgcgtat aaggctagtg ctcctggttg gccttatacg cgattaagac    60
tttttta                                                              67

<210> SEQ ID NO 38
<211> LENGTH: 67
<212> TYPE: DNA
<213> ORGANISM: Artificial Sequence
<220> FEATURE:
<223> OTHER INFORMATION: synthetic DNA

<400> SEQUENCE: 38
ctagtaaaaa agtcttaatc gcgtataagg ccaaccagga gcactagcct tatacgcgat    60
taagact                                                              67
```